United States Patent
Silverman

(10) Patent No.: US 10,113,188 B2
(45) Date of Patent: *Oct. 30, 2018

(54) COMPOSITIONS AND METHODS FOR BIOLOGICAL PRODUCTION OF FATTY ACID DERIVATIVES

(71) Applicant: Calysta, Inc., Menlo Park, CA (US)

(72) Inventor: Joshua A. Silverman, Los Altos Hills, CA (US)

(73) Assignee: Calysta, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/877,747

(22) Filed: Jan. 23, 2018

(65) Prior Publication Data

US 2018/0282769 A1    Oct. 4, 2018

Related U.S. Application Data

(63) Continuation of application No. 14/441,153, filed as application No. PCT/US2013/069252 on Nov. 8, 2013, now Pat. No. 9,909,153.

(60) Provisional application No. 61/724,733, filed on Nov. 9, 2012.

(51) Int. Cl.
| | |
|---|---|
| C12P 7/64 | (2006.01) |
| C12N 9/00 | (2006.01) |
| C12P 7/24 | (2006.01) |
| C12N 9/16 | (2006.01) |
| C12P 7/42 | (2006.01) |
| C12P 7/44 | (2006.01) |
| C12N 15/52 | (2006.01) |
| C12N 9/02 | (2006.01) |
| C12N 9/06 | (2006.01) |
| C12N 9/04 | (2006.01) |

(52) U.S. Cl.
CPC .......... *C12P 7/6409* (2013.01); *C12N 9/0006* (2013.01); *C12N 9/0008* (2013.01); *C12N 9/0026* (2013.01); *C12N 9/0077* (2013.01); *C12N 9/16* (2013.01); *C12N 9/93* (2013.01); *C12N 15/52* (2013.01); *C12P 7/24* (2013.01); *C12P 7/42* (2013.01); *C12P 7/44* (2013.01); *C12P 7/64* (2013.01); *C12P 7/6436* (2013.01); *C12Y 101/01* (2013.01); *C12Y 101/01001* (2013.01); *C12Y 102/99006* (2013.01); *C12Y 301/02* (2013.01); *C12Y 602/01* (2013.01)

(58) Field of Classification Search
None
See application file for complete search history.

(56) References Cited

U.S. PATENT DOCUMENTS

| | | | |
|---|---|---|---|
| 4,269,940 A | 5/1981 | Patel et al. | |
| 6,492,135 B1 | 12/2002 | Larsen | |
| 6,689,601 B2 | 2/2004 | Koffas et al. | |
| 6,818,424 B2 | 11/2004 | DiCosimo et al. | |
| 7,026,464 B2 | 4/2006 | Dicosimo et al. | |
| 7,098,005 B2 | 8/2006 | Dicosimo et al. | |
| 7,118,896 B2 | 10/2006 | Kalscheuer et al. | |
| 7,579,163 B2 | 8/2009 | Eriksen et al. | |
| 7,799,550 B2 | 9/2010 | Moen et al. | |
| 8,177,870 B2 | 5/2012 | Herrema et al. | |
| 8,283,143 B2 | 10/2012 | Hu et al. | |
| 8,592,198 B2 | 11/2013 | Moen et al. | |
| 2003/0003528 A1 | 1/2003 | Brzostowicz et al. | |
| 2005/0054030 A1 | 3/2005 | Schnoor et al. | |
| 2005/0163802 A1 | 7/2005 | Jorgensen et al. | |
| 2006/0057726 A1 | 3/2006 | Sharpe | |
| 2007/0065902 A1 | 3/2007 | Dicosimo et al. | |
| 2008/0026005 A1 | 1/2008 | Miguez et al. | |
| 2009/0263877 A1 | 10/2009 | Eriksen et al. | |
| 2010/0068772 A1 | 3/2010 | Downey | |
| 2010/0221813 A1 | 9/2010 | Miguez et al. | |
| 2010/0251601 A1 | 10/2010 | Hu et al. | |
| 2010/0291653 A1 | 11/2010 | Ness et al. | |
| 2010/0298612 A1 | 11/2010 | Behrouzian et al. | |
| 2011/0162259 A1* | 7/2011 | Gaertner | C10L 1/026 44/385 |
| 2011/0165639 A1 | 7/2011 | Ascon et al. | |
| 2011/0306100 A1 | 12/2011 | De Crecy | |
| 2012/0070870 A1 | 3/2012 | Way et al. | |
| 2012/0116138 A1 | 5/2012 | Goodall et al. | |
| 2012/0282663 A1 | 11/2012 | Schirmer et al. | |
| 2013/0189763 A1 | 7/2013 | Dalla-Betta et al. | |
| 2014/0013658 A1 | 1/2014 | Silverman et al. | |
| 2014/0024872 A1 | 1/2014 | Silverman et al. | |

(Continued)

FOREIGN PATENT DOCUMENTS

| | | |
|---|---|---|
| EP | 0 296 484 A2 | 12/1988 |
| EP | 1 265 982 B1 | 9/2004 |

(Continued)

OTHER PUBLICATIONS

Adas et al., "Requirement for ω and (ω-1)-hydroxylations of fatty acids by human cytochromes P450 2E1 and 4A11," *Journal of Lipid Research* 40(11):1990-1997, 1999.

Ali et al., "Duplication of the mmoX gene in *Methylosinus sporium*: cloning, sequencing and mutational analysis," *Microbiology* 152(10):2931-2942, 2006.

Barta et al., "Genetics of methane and methanol oxidation in Gram-negative methylotrophic bacteria," *Antonie van Leeuwenhoek* 64:109-120, 1993.

Benveniste et al., "CYP86A1 from *Arabidopsis thaliana* Encodes a Cytochrome P450-Dependent Fatty Acid Omega-Hydroxylase," *Biochemical and Biophysical Research Communications* 243(3):688-693, 1998.

(Continued)

*Primary Examiner* — Suzanne M Noakes
(74) *Attorney, Agent, or Firm* — Seed IP Law Group LLP

(57) ABSTRACT

The present disclosure provides compositions and methods for biologically producing fatty acid derivatives, such as fatty alcohols, from recombinant $C_1$ metabolizing microorganisms that utilize $C_1$ substrates such as methane or natural gas as a feedstock.

33 Claims, 7 Drawing Sheets

(56) References Cited

U.S. PATENT DOCUMENTS

| | | |
|---|---|---|
| 2015/0218508 A1 | 8/2015 | Silverman et al. |
| 2015/0353971 A1 | 12/2015 | Silverman et al. |

FOREIGN PATENT DOCUMENTS

| | | |
|---|---|---|
| EP | 1 497 409 B1 | 5/2006 |
| EP | 1 183 326 B1 | 3/2007 |
| EP | 1 478 376 B1 | 9/2010 |
| EP | 1 419 234 B1 | 3/2011 |
| EP | 2 455 484 A2 | 5/2012 |
| EP | 2 427 200 B1 | 4/2014 |
| WO | 01/60974 A2 | 8/2001 |
| WO | 02/18617 A2 | 3/2002 |
| WO | 03/016460 A1 | 2/2003 |
| WO | 03/068003 A1 | 8/2003 |
| WO | 03/072133 A2 | 9/2003 |
| WO | 03/089625 A2 | 10/2003 |
| WO | 2007/136762 A2 | 11/2007 |
| WO | 2008/119082 A2 | 10/2008 |
| WO | 2009/009391 A2 | 1/2009 |
| WO | 2009/140695 A1 | 11/2009 |
| WO | 2009/151342 A1 | 12/2009 |
| WO | 2010/128312 A2 | 11/2010 |
| WO | 2011/038132 A1 | 3/2011 |
| WO | 2011/044279 A2 | 4/2011 |
| WO | 2014/012055 A1 | 1/2014 |
| WO | 2014/089436 A1 | 6/2014 |
| WO | 2014/210535 A2 | 12/2014 |

OTHER PUBLICATIONS

Bligh et al., "A Rapid Method of Total Lipid Extraction and Purification, " *Canadian Journal of Biochemistry and Physiology* 37(8):911-917, 1959.

Cabello-Hurtado et al., "Cloning, Expression in Yeast, and Functional Characterization of CYP81B1, a Plant Cytochrome P450 That Catalyzes In-chain Hydroxylation of Fatty Acids," *The Journal of Biological Chemistry*, 273(13):7260-7267, 1998. (9 pages).

Cahoon et al., "Transgenic Production of Epoxy Fatty Acids by Expression of a Cytochrome P450 Enzyme from *Euphorbia lagascae* Seed," *Plant Physiology* 128(2):615-624, 2002.

Caviglia et al., "Rat Long Chain Acyl-CoA Synthetase 5, but Not 1, 2, 3, or 4, Complements *Escherichia coli* fadD," *The Journal of Biological Chemistry* 279(12):11163-11169, 2004. (8 pages).

Chen et al., "Biosynthesis of ansatrienin (mycotrienin) and naphthomycin: Identification and analysis of two separate biosynthetic gene clusters in *Streptomyces collinus* Tü 1892," *European Journal of Biochemistry*261(1):98-107, 1999.

Cheng et al., "Mammalian Wax Biosynthesis: II. Expression Cloning of Wax Synthase cDNAs Encoding A Member of the Acyltransferase Enzyme Family," *Journal of Biological Chemistry* 279(36):37798-37807, 2004. (22 pages).

Cropp et al., "Identification of a cyclohexylcarbonyl CoA biosynthetic gene cluster and application in the production of doramectin," *Nature Biotechnology* 18(9):980-983, 2000.

Darbon et al., "Antitermination by GlpP, catabolite repression via CcpA and inducer exclusion triggered by P~GlpK dephosphorylation control *Bacillus subtilis* glpFK expression," *Molecular Microbiology* 43(4):1039-1052, 2002.

de Mendoza et al., "Thermal Regulation of Membrane Fluidity in *Escherichia coli,*" *The Journal of Biological Chemistry* 258(4):2098-2101, 1983. (5 pages).

Denoya et al., "A Second Branched-Chain α-Keto Acid Dehydrogenase Gene Cluster (*bkdFGH*) from *Streptomyces avermitilis*: Its Relationship to Avermectin Biosynthesis and the Construction of a *bkdF* Mutant Suitable for the Production of Novel Antiparasitic Avermectins," *Journal of Bacteriology* 177(12):3504-3511, 1995.

Fang et al., "Characterization of methanotrophic bacteria on the basis of intact phospholipid profiles," *FEMS Microbiology Letters* 189(1):67-72, 2000.

Folch et al., "A Simple Method for the Isolation and Purification of Total Lipides From Animal Tissues," *Journal of Biological Chemistry* 226(1):497-509, 1957.

Han et al., "A Novel Alternate Anaplerotic Pathway to the Glyoxylate Cycle in Streptomycetes," *Journal of Bacteriology* 179(16):5157-5164, 1997.

Hanson et al., "Methanotrophic Bacteria," *Microbiological Reviews* 60(2):439-471, 1996.

Hardwick, "Cytochrome P450 omega hydroxylase (CYP4) function in fatty acid metabolism and metabolic diseases," *Biochemical Pharmacology* 75(12):2263-2275, 2008.

Heath et al., "Lipid biosynthesis as a target for antibacterial agents," *Progress in Lipid Research* 40(6):467-497, 2001.

Helm et al., "Characterizing a stable methane-utilizing mixed culture used in the synthesis of a high-quality biopolymer in an open system," *Journal of Applied Microbiology* 101(2):387-395, 2006.

Henstra et al., "Microbiology of synthesis gas fermentation for biofuel production," *Current Opinion in Biotechnology* 18(3):200-206, 2007.

Jahnke et al., "Evidence for the synthesis of the multi-positional isomers of monounsaturated fatty acid in *Methylococcus capsusatus* by the anaerobic pathway," *FEMS Microbiology Letters* 58:183-188, 1989.

Jahnke, "The effects of growth temperature on the methyl sterol and phospholipid fatty acid composition of *Methylococcus capsulatus* (Bath), " *FEMS Microbiology Letters* 93(3):209-212, 1992.

Kalscheuer et al., "A Novel Bifunctional Wax Ester Synthase/Acyl-CoA:Diacylglycerol Acyltransferase Mediates Wax Ester and Triacylglycerol Biosynthesis in *Acinetobacter calcoaceticus* ADP1," *The Journal of Biological Chemistry* 278(10):8075-8082, 2003. (9 pages).

Kalscheuer et al., "Microdiesel: *Escherichia coli* engineered for fuel production," *Microbiology* 152(9):2529-2536, 2006.

Kalyuzhnaya et al., "Metabolic engineering in methanotrophic bacteria," *Metabolic Engineering* 29:142-152, 2015.

Kandel et al., "Cloning, Functional Expression, and Characterization of CYP709C1, the First Sub-terminal Hydroxylase of Long Chain Fatty Acid in Plants," *The Journal of Biological Chemistry* 280(43):35881-35889, 2005. (10 pages).

Kaneda, "Iso- and Anteiso-Fatty Acids in Bacteria: Biosynthesis, Function, and Taxonomic Significance," *Microbiological Reviews* 55(2):288-302, 1991.

Keeling et al., "Monthly Atmospheric $^{13}C/^{12}C$ Isotopic Ratios for 11 SIO Stations," Trends: A Compendium of Data on Global Change. Carbon Dioxide Information Analysis Center, Oak Ridge National Laboratory, U.S. Department of Energy, Oak Ridge, Tennessee, USA, Feb. 16, 2010, 3 pages.

Kendall et al., "Resources on Isotopes: Periodic Table—Carbon," Isotope Tracers Project, URL=http://wwwrcamnl.wr.usgs.gov/isoig/period/c_iig.html, download date Nov. 23, 2015. (4 pages).

Kosa et al., "Lipids from heterotrophic microbes: advances in metabolism research," *Trends in Biotechnology* 29(2):53-61, 2011.

Larkin, "Isolation of a cytochrome P450 homologue preferentially expressed in developing inflorescences of *Zea Mays, "Plant Molecular Biology* 25(3):343-353, 1994. (13 pages).

Le Bouquin et al., "CYP94A5, a new cytochrome P450 from *Nicotiana tabacum* is able to catalyze the oxidation of fatty acids to the ω-alcohol and to the corresponding diacid," *European Journal of Biochemistry* 268(10):3083-3090, 2001.

Lee et al., "Substrate Recognition and Molecular Mechanism of Fatty Acid Hydroxylation by Cytochrome P450 from *Bacillus subtilis,"* *The Journal of Biological Chemistry* 278(11):9761-9767, 2003. (8 pages).

Lee et al., "Heterologous Co-expression of *accA, fabD*, and Thioesterase Genes for Improving Long-Chain Fatty Acid Production in *Pseudomonas aeruginosa* and *Escherichia coli,"* *Applied Biochemistry and Biotechnology* 167(1):24-38, 2012.

Li et al., "Alteration of the Fatty Acid Profile of *Streptomyces coelicolor* by Replacement of the Initiation Enzyme 3-Ketoacyl Acyl Carrier Protein Synthase III (FabH)," *Journal of Bacteriology* 187(11):3795-3799, 2005.

Liu et al., "Advances in phosphopantetheinyl transferase," *Chinese Journal of Antibiotics* 31(6):335-338, 2006. (English Abstract Only).

(56) References Cited

OTHER PUBLICATIONS

Lloyd et al., "Heterologous expression of soluble methane monooxygenase genes in methanotrophs containing only particulate methane monooxygenase," *Archives of Microbiology* 171(6):364-370, 1999.
Marrakchi et al., "A New Mechanism for Anaerobic Unsaturated Fatty Acid Formation in *Streptococcus pneumoniae*," *The Journal of Biological Chemistry* 277(47):44809-44816, 2002. (9 pages).
Marrakchi et al., "Mechanistic diversity and regulation of Type II fatty acid synthesis," *Biochemical Society Transactions* 30(6):1050-1055, 2002.
Matsunaga et al., "Fatty Acid-Specific, Regiospecific, and Stereospecific Hydroxylation by Cytochrome P450 (CYP152B1) from *Sphingomonas paucimobilis*: Substrate Structure Required for α-hydroxylation," *Lipids* 35(4):365-371, 2000.
Metz et al., "Purification of a Jojoba Embryo Fatty Acyl-Coenzyme A Reductase and Expression of Its cDNA in High Erucic Acid Rapeseed," *Plant Physiology* 122(3):635-644, 2000.
Nelson, "Isolation and Purification of Lipids from Animal Tissues," in Perkins (ed.), *Analysis of Lipids and Lipoproteins*, American Oil Chemists' Society, Champaign, Illinois, USA, 1975, pp. 1-22.
Nichols et al., "Phospholipid and lipopolysaccharide normal and hydroxy fatty acids as potential signatures for methane-oxidizing bacteria," *FEMS Microbiology Ecology* 0:327-335, 1985.
Oliver et al., "A Single Mutation in Cytochrome P450 BM3 Changes Substrate Orientation in a Catalytic Intermediate and the Regiospecificity of Hydroxylation," *Biochemistry* 36(7):1567-1572, 1997.
Palaniappan et al., "Enhancement and Selective Production of Phoslactomycin B, a Protein Phosphatase IIa Inhibitor, through Identification and Engineering of the Corresponding Biosynthetic Gene Cluster," *The Journal of Biological Chemistry* 278(37):35552-35557, 2003. (7 pages).
Park et al., "Metabolic Fractionation of $C^{13}$ & $C^{12}$ in Plants," *Plant Physiology* 36(2):133-138, 1961.
Patton et al., "A Novel $\Delta^3,\Delta^2$-Enoyl-CoA Isomerase Involved in the Biosynthesis of the Cyclohexanecarboxylic Acid-Derived Moiety of the Polyketide Ansatrienin A," *Biochemistry* 39(25):7595-7604, 2000.
Petkova-Andonova et al., "CYP9281, A Cytochrome P450, Expressed in Petunia Flower Buds, That Catalyzes Monooxidation of Long-Chain Fatty Acids," *Bioscience, Biotechnology and Biochemistry* 66(9):1819-1828, 2002.
Prather et al., "*De Novo* biosynthetic pathways: rational design of microbial chemical factories," *Current Opinion in Biotechnology* 19:468-474, 2008.
Rock et al., "Increased Unsaturated Fatty Acid Production Associated with a Suppressor of the *fabA6*(Ts) Mutation in *Escherichia coli*," *Journal of Bacteriology* 178(18):5382-5387, 1996.
Schrader et al., "Methanol-based industrial biotechnology: current status and future perspectives of methylotrophic bacteria," *Trends in Biotechnology* 27(2):107-115, 2009.
Sharp et al., "Variation in the strength of selected codon usage bias among bacteria," *Nucleic Acids Research* 33(4):1141-1153, 2005.
Shirane et al., "Cytochrome $P450_{BM-3}$ (CYP102): Regiospecificity of Oxidation of ω-Unsaturated Fatty Acids and Mechanism-Based Inactivation," *Biochemistry* 32(49):13732-13741, 1993.
Shockey et al., "Arabidopsis Contains Nine Long-Chain Acyl-Coenzyme A Synthetase Genes That Participate in Fatty Acid and Glycerolipid Metabolism," *Plant Physiology* 129(4):1710-1722, 2002.
Springer et al., "Sequence and characterization of *mxaB*, a response regulator involved in regulation of methanol oxidation, and of *mxaW*, a methanol-regulated gene in *Methylobacterium extorquens* AM1," *FEMS Microbiology Letters* 160(1):119-124, 1998.
Stein et al., "Genome Sequence of the Obligate Methanotroph *Methylosinus trichosporium* Strain OB3b," *Journal of Bacteriology* 192(24):6497-6498, 2010.
Stolyar et al., "Role of multiple gene copies in particulate methane monooxygenase activity in the methane-oxidizing bacterium *Methylococcus capsulatus* Bath," *Microbiology* 145(5):1235-1244, 1999.
Summons et al., "Carbon isotopic fractionation in lipids from methanotrophic bacteria: Relevance for interpretation of the geochemical record of biomarkers," *Geochimica et Cosmochimica Acta* 58(13):2853-2863, 1994.
Templeton et al., "Variable carbon isotope fractionation expressed by aerobic $CH_4$-oxidizing bacteria," *Geochimica et Cosmochimica Acta* 70(7):1739-1752, 2006.
Terekhova et al., "Stearic Acid Methyl Ester: A New Extracellular Metabolite of the Obligate Methylotrophic Bacterium *Methylophilus quaylei*," *Applied Biochemistry and Microbiology* 46(2): 166-172, 2010.
Tijet et al., "Functional expression in yeast and characterization of a clofibrate-inducible plant cytochrome *P*-450 (CYP94A1) involved in cutin monomers synthesis," *Biochemical Journal* 332(2):583-589, 1998.
Wellesen et al., "Functional analysis of the *LACERATA* gene of *Arabidopsis* provides evidence for different roles of fatty acid ω-hydroxylation in development," *Proceedings of the National Academy of Sciences of the United States of America* 98(17):9694-9699, 2001.
Whiticar et al., "Methane oxidation in sediment and water column environments—Isotope evidence," *Advances in Organic Geochemistry* 10(4-6):759-768, 1986.
Whiticar, "A geochemial perspective of natural gas and atmospheric methane, "*Advances in Organic Geochemistry* 16(1-3):531-547, 1990.
Younesi et al., "Ethanol and acetate production from synthesis gas via fermentation processes using anaerobic bacterium, *Clostridium ljungdahlii*," *Biochemical Engineering Journal* 27:110-119, 2005.
Zhang et al., "The FabR (YijC) Transcription Factor Regulates Unsaturated Fatty Acid Biosynthesis in *Escherichia coli*," *The Journal of Biological Chemistry* 277(18): 15558-15565, 2002. (9 pages).

* cited by examiner

COMPOSITIONS AND METHODS FOR BIOLOGICAL PRODUCTION OF FATTY ACID DERIVATIVES

BACKGROUND

Technical Field

The present disclosure provides compositions and methods for biologically producing fatty acid derivatives and, more specifically, using recombinant $C_1$ metabolizing microorganisms to produce fatty alcohols, hydroxy fatty acids, or dicarboxylic acids from $C_1$ substrates (such as methane or natural gas).

Background Description

Fatty alcohols are aliphatic alcohols that are predominantly linear and monohydric. They are composed of a nonpolar lipophilic, saturated or unsaturated hydrocarbon chain, usually from $C_6$ to $C_{24}$, and a polar, hydrophilic hydroxyl group attached to the terminal carbon. Fatty alcohols are high value chemicals with a multitude of applications, such as surfactants, detergents, lubricant additives, defoamers, solubility retarders, and consistency giving factors. Fatty alcohol production capacity was approximately 2 million metric tons per year in 2009. Included in the capacity are $C_{12}/C_{14}$ alcohols, $C_{16}/C_{18}$ alcohols, and $C_{15}/C_{18}$ alcohols. The global surfactant market is expected to reach $16.65 billion by 2012. Nonionic surfactants constitute the second largest group of products in the surfactant market. Fatty acid based surfactants represent some 20% of the nonionic type of surfactants.

Currently the fatty alcohol market is dominated by natural alcohol and synthetic alcohol products. Natural alcohols are prepared from natural oils, fats, and waxes of plants or animals, such as coconut or palm oil, using transesterification and hydrogenation processes. Synthetic alcohols are produced from petrochemical feedstocks such as ethene, olefins and paraffins, mainly from the Ziegler alcohol process, SHOP process, and Oxo process. However, these processes either require harsh production environments, questionable land use practices, or environmentally detrimental byproducts.

Increasing efforts have been made to enable microbial production of fatty alcohols from abundant and cost-effective renewable resources. In particular, recombinant microorganisms, such as *E. coli* and various yeasts, have been used to convert biomass-derived feedstocks to fatty alcohols, such as lauryl alcohol. However, even with the use of relatively inexpensive cellulosic biomass as a feedstock, more than half the mass of carbohydrate feedstocks is comprised of oxygen, which represents a significant limitation in conversion efficiency. Long chain fatty acids and their derivatives (such as fatty alcohols, hydroxy-fatty acids, fatty aldehydes,) have significantly lower oxygen content than the feedstocks, which limits the theoretical yield as the oxygen must be eliminated as waste. Thus, the economics of production of fatty acids and their derivatives from carbohydrate feedstocks is prohibitively expensive.

In view of the limitations associated with carbohydrate-based fermentation methods for production of fatty alcohol and related compounds, there is a need in the art for alternative, cost-effective, and environmentally friendly methods for producing fatty alcohols. The present disclosure meets such needs, and further provides other related advantages.

BRIEF SUMMARY

In certain aspects, the present disclosure is directed to a method for making a fatty acid derivative by culturing a non-natural $C_1$ metabolizing non-photosynthetic microorganism with a $C_1$ substrate feedstock and recovering the fatty acid derivative, wherein the $C_1$ metabolizing non-photosynthetic microorganism comprises a recombinant nucleic acid molecule encoding a fatty acid converting enzyme, and wherein the $C_1$ metabolizing non-photosynthetic microorganism converts the $C_1$ substrate into a $C_8$-$C_{24}$ fatty acid derivative comprising a fatty aldehyde, a fatty alcohol, a hydroxy fatty acid, a dicarboxylic acid, or a combination thereof.

In a related aspect, the present disclosure provides a non-natural methanotroph, comprising a recombinant nucleic acid molecule encoding a fatty acid converting enzyme, wherein the methanotroph is capable of converting a $C_1$ substrate into a $C_8$-$C_{24}$ fatty aldehyde, fatty alcohol, fatty ester wax, a hydroxy fatty acid, dicarboxylic acid, or a combination thereof. In certain embodiments, there are provided non-natural methanotrophs containing a recombinant nucleic acid molecule encoding a heterologous acyl-CoA dependent or independent fatty acyl-CoA reductase, a recombinant nucleic acid molecule encoding a heterologous thioesterase, and a recombinant nucleic acid molecule encoding a heterologous acyl-CoA synthetase, wherein the methanotroph is capable of converting a $C_1$ substrate into a $C_8$-$C_{24}$ fatty alcohol.

In further embodiments, there are provided non-natural methanotrophs containing a recombinant nucleic acid molecule encoding a carboxylic acid reductase, a recombinant nucleic acid molecule encoding a phosphopantetheinyl tranferase, and a recombinant nucleic acid molecule encoding an alcohol dehydrogenase, wherein the methanotroph is capable of converting a $C_1$ substrate into a $C_8$-$C_{24}$ fatty alcohol.

In still further embodiments, provided are non-natural methanotrophs containing a recombinant nucleic acid molecule encoding a heterologous fatty acyl-CoA reductase, a recombinant nucleic acid molecule encoding a heterologous thioesterase, and a recombinant nucleic acid molecule encoding a heterologous P450 or monooxygenase, wherein the native alcohol dehydrogenase is inhibited and the methanotroph is capable of converting a $C_1$ substrate into a $C_8$-$C_{24}$ ω-hydroxy fatty acid.

In yet further embodiments, there are provided non-natural methanotrophs containing a recombinant nucleic acid molecule encoding a heterologous fatty acyl-CoA reductase, and a recombinant nucleic acid molecule encoding a heterologous thioesterase, wherein the methanotroph is over-expressing native alcohol dehydrogenase as compared to the normal expression level of native alcohol dehydrogenase, transformed with a recombinant nucleic acid molecule encoding a heterologous alcohol dehydrogenase, or both, and wherein the methanotroph is capable of converting a $C_1$ substrate into a $C_8$-$C_{24}$ dicarboxylic acid alcohol.

In another aspect, the present disclosure provides a $C_1$ metabolizing microorganism biomass comprising a fatty acid derivative composition, wherein the fatty acid derivative containing biomass or a fatty acid derivative composition therefrom has a $\delta^{13}C$ of about −35‰ to about −50‰, −45‰ to about −35‰, or about −50‰ to about −40‰, or about −45‰ to about −65‰, or about −60‰ to about −70‰, or about −30‰ to about −70‰. In certain embodiments, a fatty acid derivative composition comprises fatty aldehyde, fatty alcohol, fatty ester wax, hydroxy fatty acid, dicarboxylic acid, or any combination thereof. In still further embodiments, a fatty acid derivative composition comprises $C_8$-$C_{24}$ fatty alcohol, $C_8$-$C_{24}$ branched chain fatty alcohol, $C_8$-$C_{24}$ fatty aldehyde, $C_8$-$C_{24}$ ω-hydroxy fatty acid, or $C_8$-$C_{24}$ dicarboxylic acid alcohol. In yet further embodiments, a fatty acid derivative composition comprises a majority (more than 50% w/w) of fatty acids having carbon chain lengths ranging from $C_8$ to $C_{14}$ or from $C_{10}$ to $C_{16}$ or from $C_{14}$ to $C_{24}$, or a majority of fatty acid derivatives having carbon chain lengths of less than $C_{18}$, or a fatty alcohol containing composition wherein at least 70% of the total fatty alcohol comprises $C_{10}$ to $C_{18}$ fatty alcohol.

DETAILED DESCRIPTION

Figure 1:
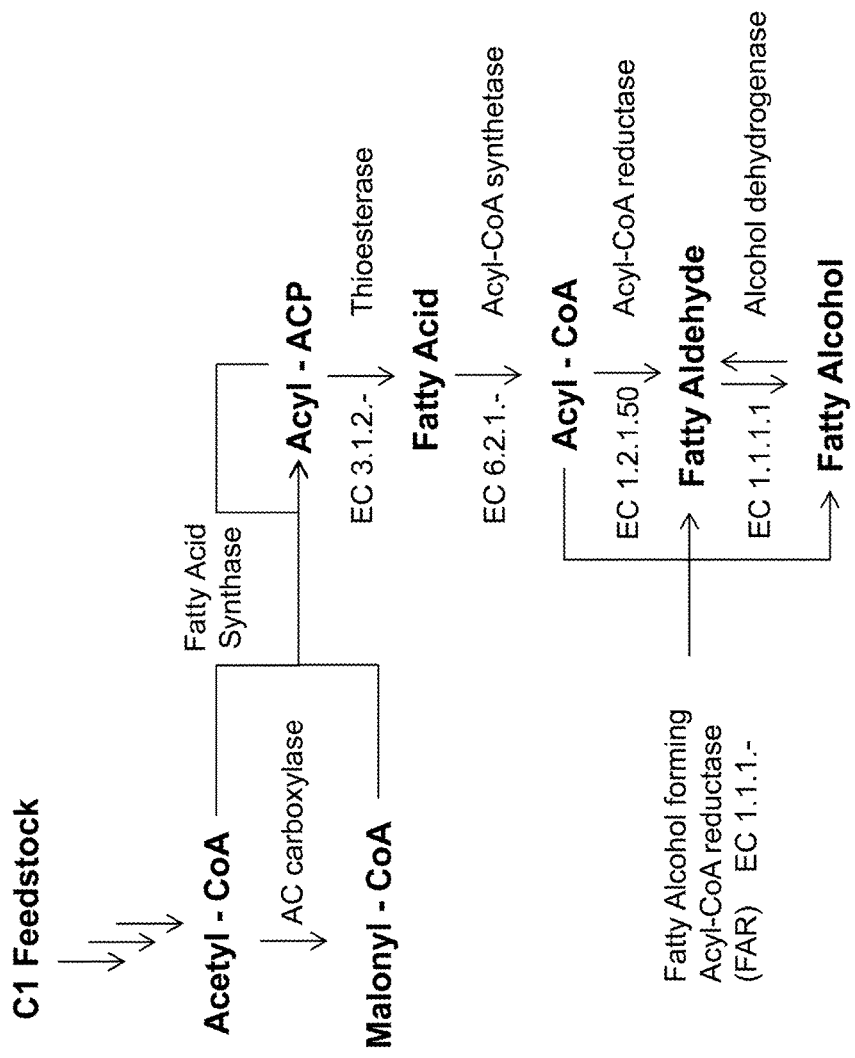
FIG. 1 shows an overview of an acyl-CoA dependent FAR Pathway for fatty alcohol production.
Figure 2:
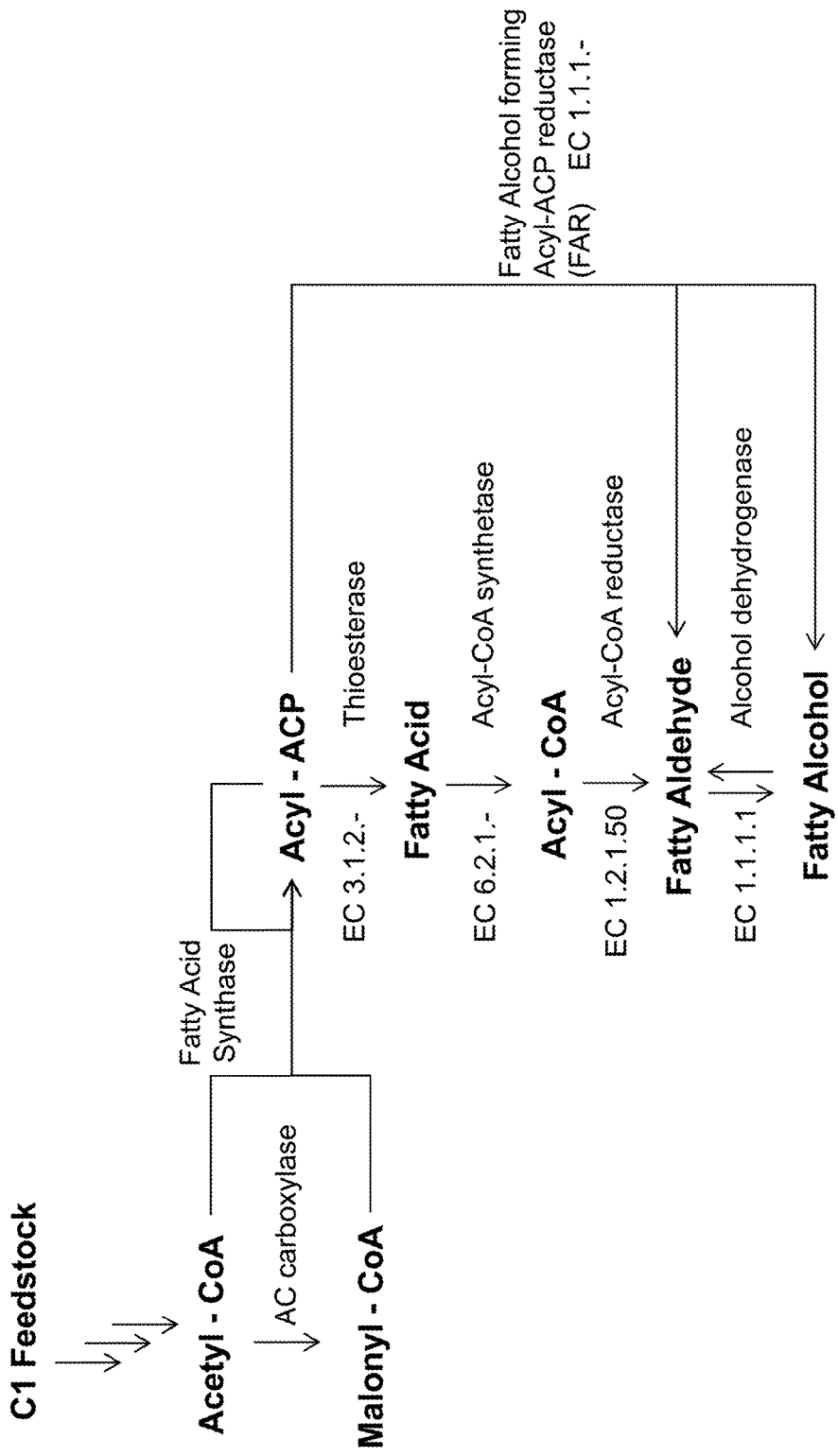
FIG. 2 shows an overview of an acyl-CoA independent FAR pathway for fatty alcohol production.
Figure 3:
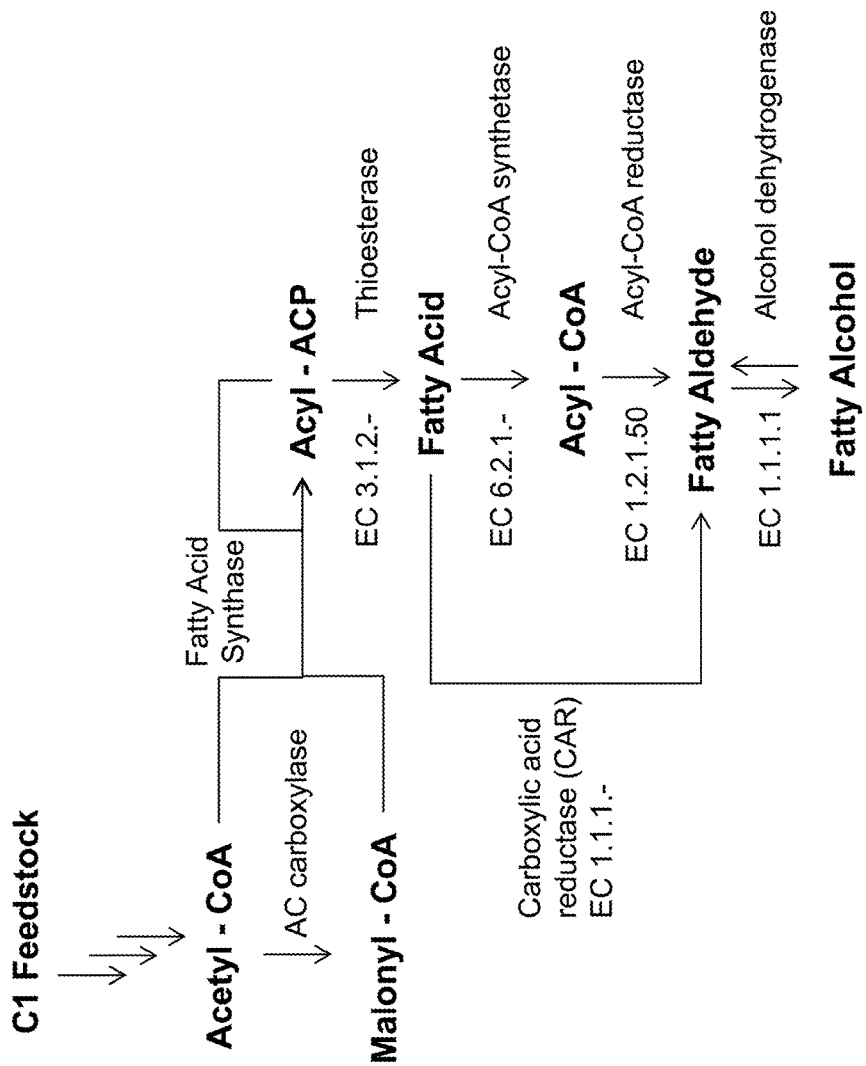
FIG. 3 shows an overview of an acyl-CoA independent CAR pathway for fatty alcohol production.
Figure 4:
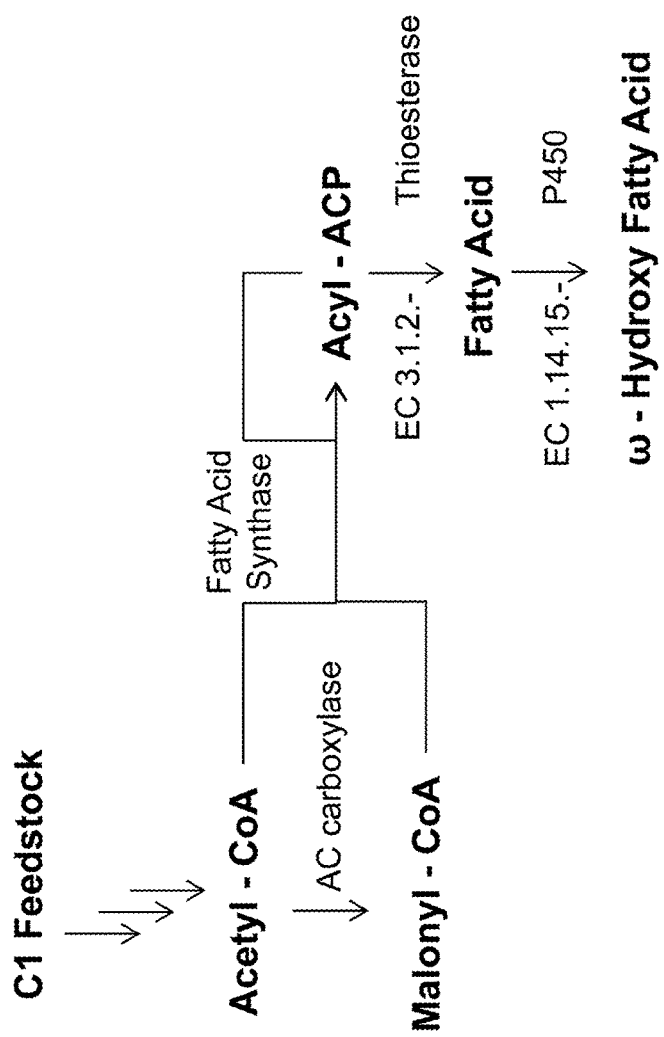
FIG. 4 shows an overview of a ω-hydroxy fatty acid production pathway.
Figure 5:
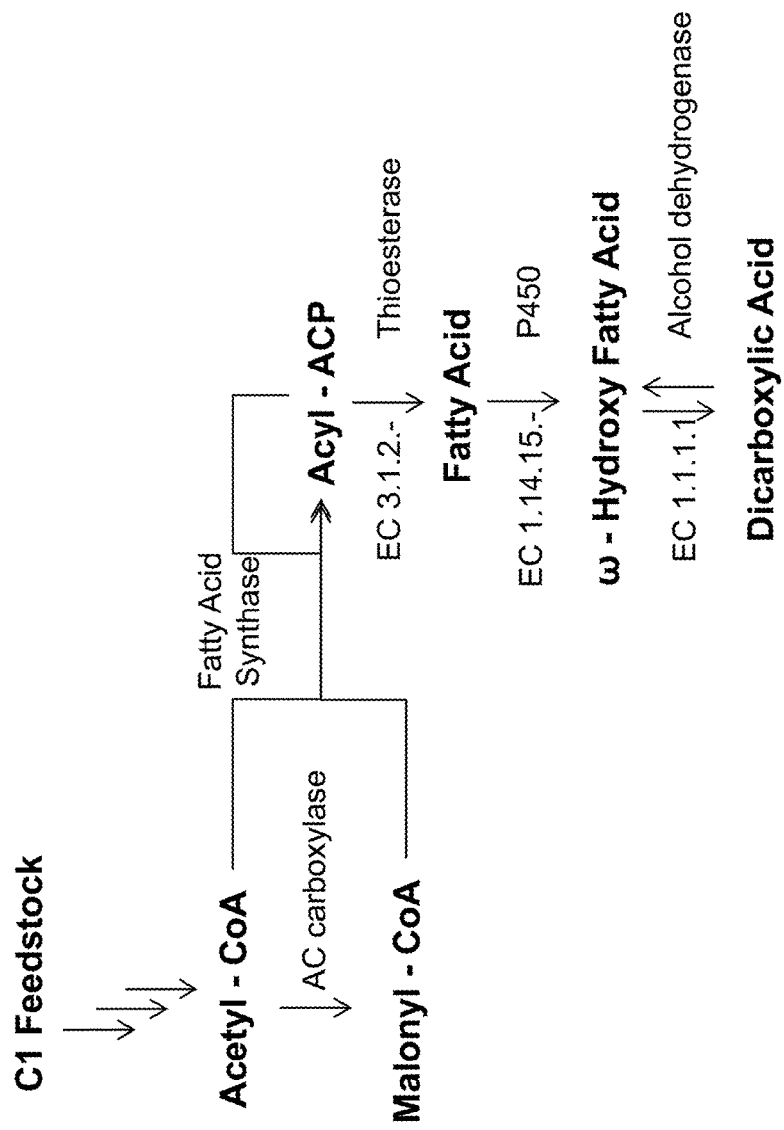
FIG. 5 shows an overview of a dicarboxylic acid production pathway.
Figure 6:
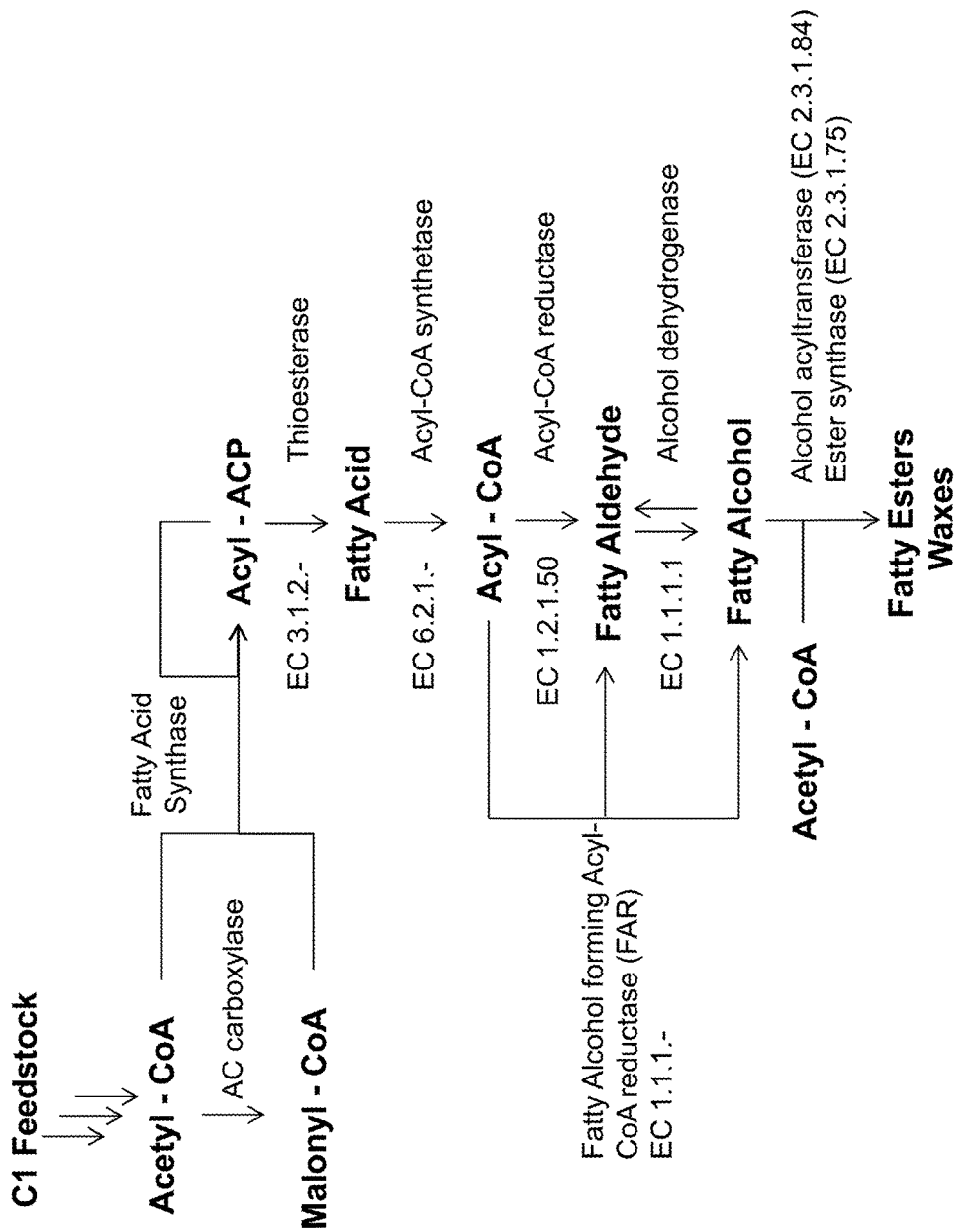
FIG. 6 shows an overview of an acyl-CoA dependent FAR pathway for fatty ester production.

The instant disclosure provides compositions and methods for generating fatty acid derivatives. For example, recombinant $C_1$ metabolizing microorganisms are cultured with a $C_1$ substrate feedstock (e.g., methane) to generate $C_8$ to $C_{24}$ fatty aldehyde, fatty alcohol, fatty ester wax, hydroxy fatty acid, dicarboxylic acid, or any combination thereof. This new approach allows for the use of methylotroph or methanotroph bacteria as a new host system to generate fatty acid derivatives for use in producing, for example, surfactants, lubricants, solvents, or detergents.

By way of background, methane from a variety of sources, including natural gas, represents an abundant domestic resource. As noted above, carbohydrate based feedstocks contain more than half of their mass in oxygen, which is a significant limitation in conversion efficiency as long chain fatty alcohols have significantly lower oxygen content than these feedstocks. A solution to address the limitations of current systems is to utilize methane or natural gas as a feedstock for conversion. Methane from natural gas is cheap and abundant, and importantly contains no oxygen, which allows for significant improvements in theoretical conversion efficiency. Furthermore, $C_1$ carbon sources are cheap and abundant compared to carbohydrate feedstocks, which also contributes to improved economics of fatty alcohol production.

Fatty acid production is an important pathway in virtually all organisms as it is required for membrane biosynthesis. In the present disclosure, metabolic engineering techniques are applied to increase overall carbon flux to the production of fatty acids, for example, by over-expressing genes associated with fatty acid biosynthesis (e.g., acyl-coA synthase, acetyl-coA carboxylase, acyl carrier protein, pyruvate dehydrogenase) while simultaneously inhibiting, down-regulating or eliminating enzymes associated with fatty acid degradation or competing metabolic pathways. In additional embodiments, the composition and chain length of fatty acids are controlled by introducing heterologous thioesterase genes that are specific for a desired chain length while optionally inhibiting, down-regulating or eliminating native thioesterase genes (e.g., in bacteria, introducing fatB1 thioesterase from *Umbellularia californica*, which selectively produces $C_{12}$ fatty acid chains, and eliminating the native thioesterases that typically produce chain lengths of $C_{16}$-$C_{18}$ in bacteria). In still further embodiments, branched chain fatty acids are produced by introduction of various enzymes in the branched chain α-ketoacid synthesis pathway (branched chains also provide significant advantages for some surfactant and detergent applications).

In one aspect, the present disclosure provides a method for a fatty acid derivative, comprising culturing a non-natural $C_1$ metabolizing non-photosynthetic microorganism in the presence of a $C_1$ substrate feedstock and recovering the fatty acid derivative, wherein the $C_1$ metabolizing non-photosynthetic microorganism comprises a recombinant nucleic acid molecule encoding a fatty acid converting enzyme, and wherein the $C_1$ metabolizing non-photosynthetic microorganism converts the $C_1$ substrate into a $C_8$-$C_{24}$ fatty acid derivative comprising a fatty aldehyde, a fatty alcohol, a fatty ester wax, a hydroxy fatty acid, a dicarboxylic acid, or a combination thereof. In another aspect, this disclosure provides a non-natural methanotroph that includes a recombinant nucleic acid molecule encoding a fatty acid converting enzyme, wherein the methanotroph is capable of converting a $C_1$ substrate into a $C_8$-$C_{24}$ fatty aldehyde, fatty alcohol, fatty ester wax, hydroxy fatty acid, dicarboxylic acid, or a combination thereof.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, the term "recombinant" or "non-natural" refers to an organism, microorganism, cell, nucleic acid molecule, or vector that includes at least one genetic alternation or has been modified by the introduction of an exogenous nucleic acid, or refers to a cell that has been altered such that the expression of an endogenous nucleic acid molecule or gene can be controlled, where such alterations or modifications are introduced by genetic engineering. Genetic alterations include, for example, modifications introducing expressible nucleic acid molecules encoding proteins or enzymes, other nucleic acid additions, nucleic acid deletions, nucleic acid substitutions, or other functional disruption of the cell's genetic material. Such modifications include, for example, coding regions and functional fragments thereof for heterologous or homologous polypeptides for the referenced species. Additional modifications include, for example, non-coding regulatory regions in which the modifications alter expression of a gene or operon. Exemplary proteins or enzymes include proteins or enzymes (i.e., components) within a fatty acid biosynthesis pathway (e.g., fatty acyl-CoA reductase, a thioesterase, acyl-CoA synthetase, or a combination thereof). Genetic modifications to nucleic acid molecules encoding enzymes, or functional fragments thereof, can confer a biochemical reaction capability or a metabolic pathway capability to the recombinant cell that is altered from its naturally occurring state.

The following abbreviations of enzyme names are used herein: "fatty acyl reductase" or "fatty alcohol forming acyl-CoA reductase" is referred to as "FAR"; "acyl carrier protein" is referred to as "ACP"; "coenzyme A" is referred to as "CoA"; "thioesterase" is referred to as "TE"; "fatty acid synthase" or "fatty acid synthetase" is referred to as "FAS"; "fatty acyl-CoA reductase" is referred to as "FACR"; "fatty acyl-CoA synthase" or "fatty acyl-CoA synthetase" or "acyl-CoA synthase" or "acyl-CoA synthetase" are used interchangeably herein and are referred to as "FACS"; and "acetyl-CoA carboxylase" is referred to as "ACC".

Fatty Acyl Reductase (FAR), as shown in FIG. 1 and used herein, refers to an enzyme that catalyzes the reduction of a fatty acyl-CoA, a fatty acyl-ACP, or other fatty acyl thioester complex (each having a structure of R—(CO)—S—$R_1$, Formula I) to a fatty alcohol (structure R—OH, Formula II). For example, R—(CO)—S—$R_1$ (Formula I) is converted to R—OH (Formula II) and $R_1$—SH (Formula III) when two molecules of NADPH are oxidized to $NADP^+$, wherein R is a $C_8$ to $C_{24}$ saturated, unsaturated, linear, branched or cyclic hydrocarbon, and $R_1$ represents CoA, ACP or other fatty acyl thioester substrate. CoA is a non-protein acyl carrier group involved in the synthesis and oxidation of fatty acids. "ACP" is a polypeptide or protein subunit of FAS used in the synthesis of fatty acids. FARs are distinct from FACRs. FACRs reduce only fatty acyl-CoA intermediates to fatty aldehydes and require an additional oxidoreductase enzyme to generate the corresponding fatty alcohol. Fatty aldehyde, as used herein (see FIG. 1), refers to a saturated or unsaturated aliphatic aldehyde, wherein R is as defined above.

The term "fatty acid" as used herein refers to a compound of structure R—COOH (Formula IV), wherein R is a $C_8$ to $C_{24}$ saturated, unsaturated, linear, branched or cyclic hydrocarbon and the carboxyl group is at position 1. Saturated or unsaturated fatty acids can be described as "Cx:y", wherein "x" is an integer that represents the total number of carbon atoms and "y" is an integer that refers to the number of double bonds in the carbon chain. For example, a fatty acid referred to as C12:0 or 1-dodecanoic acid means the compound has 12 carbons and zero double bonds.

The term "hydroxyl fatty acid" as used herein refers to a compound of structure OH—R—COOH (Formula V), wherein R is a $C_8$ to $C_{24}$ saturated, unsaturated, linear, branched or cyclic hydrocarbon. Omega hydroxy fatty acids (also known as ω-hydroxy acids) are a class of naturally occurring straight-chain aliphatic organic acids having a certain number of carbon atoms long with the carboxyl group at position 1 and a hydroxyl at position n. For example, exemplary $C_{16}$ ω-hydroxy fatty acids are 16-hydroxy palmitic acid (having 16 carbon atoms, with the carboxyl group at position 1 and the hydroxyl group at position 16) and 10,16-dihydroxy palmitic acid (having 16 carbon atoms, with the carboxyl group at position 1, a first hydroxyl group at position 10, and a second hydroxyl group at position 16).

The term "fatty alcohol" as used herein refers to an aliphatic alcohol of Formula II, wherein R is a $C_8$ to $C_{24}$ saturated, unsaturated, linear, branched or cyclic hydrocarbon. Saturated or unsaturated fatty alcohols can be described as "Cx:y-OH", wherein "x" is an integer that represents the total number of carbon atoms in the fatty alcohol and "y" is an integer that refers to the number of double bonds in carbon chain.

Unsaturated fatty acids or fatty alcohols can be referred to as "cis$\Delta^z$" or "trans$\Delta^z$", wherein "cis" and "trans" refer to the carbon chain configuration around the double bond and "z" indicates the number of the first carbon of the double bond, wherein the numbering begins with the carbon having the carboxylic acid of the fatty acid or the carbon bound to the —OH group of the fatty alcohol.

The term "fatty acyl-thioester" or "fatty acyl-thioester complex" refers to a compound of Formula I, wherein a fatty acyl moiety is covalently linked via a thioester linkage to a carrier moiety. Fatty acyl-thioesters are substrates for the FAR enzymes described herein.

The term "fatty acyl-CoA" refers to a compound of Formula I, wherein $R_1$ is Coenzyme A, and the term "fatty acyl-ACP" refers to a compound of Formula I, wherein $R_1$ is an acyl carrier protein ACP).

The phrase "acyl-CoA independent pathway" refers to the production of fatty alcohols by the direct enzymatic conversion of fatty acyl-ACP substrates to fatty alcohols and does not involve the use of free fatty acids or fatty acyl-CoA intermediates. This biosynthetic pathway differs from two types of fatty acyl-CoA dependent pathways—one that converts fatty acyl-ACP directly to fatty acyl CoA via an acyl-transfer reaction, and a second that converts fatty acyl-ACP to fatty acyl-CoA via a free fatty acid intermediate (see FIG. 1). The acyl-CoA independent pathway has the advantage of bypassing the step of form a fatty acyl-CoA substrate from free fatty acid, which requires the use of ATP. Therefore, the acyl-CoA independent pathway may use less energy than the acyl-CoA dependent pathway that utilizes a free fatty acid intermediate.

As used herein, "alcohol dehydrogenase" (ADH) refers to any enzyme capable of converting an alcohol into its corresponding aldehyde, ketone, or acid. An alcohol dehydrogenase may have general specificity, capable of converting at least several alcohol substrates, or may have narrow specificity, accepting one, two or a few alcohol substrates.

As used herein, "particulate methane monooxygenase" (pMMO) refers to a membrane-bound particulate enzyme that catalyzes the oxidation of methane to methanol in methanotrophic bacteria. The term pMMO means either the multi-component enzyme or the subunit comprising the enzyme's active site.

As used herein, "soluble methane monooxygenase" (sMMO) refers to an enzyme found in the soluble fraction of cell lysates (cytoplasm) that catalyzes the oxidation of methane to methanol in methanotrophic bacteria. The term sMMO means either the multi-component enzyme or the subunit comprising the enzyme's active site.

As used herein, "P450," also known as "cytochrome P450" or "CYP," refers to a group of enzymes with broad substrate specificity that catalyze the oxidation of organic compounds, including lipids, steroidal hormones, and xenobiotic substances. The P450 enzyme most commonly catalyzes a monooxygenase reaction by inserting an oxygen atom into the R—H bond of an organic substrate.

"Conversion" refers to the enzymatic conversion of a substrate to one or more corresponding products. "Percent conversion" refers to the percent of substrate that is reduced to one or more products within a period of time under specified conditions. Thus, the "enzymatic activity" or "activity" of a polypeptide enzyme can be expressed as "percent conversion" of a substrate to product.

As used herein, the term "host" refers to a microorganism (e.g., methanotroph) that is being genetically modified with fatty acid biosynthesis components (e.g., thioesterase, fatty acyl-CoA reductase) to convert a $C_1$ substrate feedstock into a $C_8$-$C_{24}$ fatty aldehyde, fatty alcohol, fatty ester wax, a hydroxy fatty acid, dicarboxylic acid, or any combination thereof. A host cell may already possess other genetic modifications that confer desired properties unrelated to the fatty acid biosynthesis pathway disclosed herein. For example, a host cell may possess genetic modifications conferring high growth, tolerance of contaminants or particular culture conditions, ability to metabolize additional carbon substrates, or ability to synthesize desirable products or intermediates.

As used herein, the term "methanotroph," "methanotrophic bacterium" or "methanotrophic bacteria" refers to a methylotrophic bacteria capable of utilizing $C_1$ substrates, such as methane or unconventional natural gas, as its primary or sole carbon and energy source. As used herein, "methanotrophic bacteria" include "obligate methanotrophic bacteria" that can only utilize $C_1$ substrates for carbon and energy sources and "facultative methanotrophic bacteria" that are naturally able to use multi-carbon substrates, such as acetate, pyruvate, succinate, malate, or ethanol, in addition to $C_1$ substrates as their sole carbon and energy source. Facultative methanotrophs include some species of *Methylocella, Methylocystis*, and *Methylocapsa* (e.g., *Methylocella silvestris, Methylocella palustris, Methylocella tundrae, Methylocystis daltona* SB2, *Methylocystis bryophila*, and *Methylocapsa aurea* KYG), and *Methylobacterium organophilum* (ATCC 27,886).

As used herein, the term "$C_1$ substrate" or "$C_1$ compound" refers to an organic compound having lacking carbon to carbon bonds. $C_1$ substrates include syngas, natural gas, unconventional natural gas, methane, methanol, formaldehyde, formic acid (formate), carbon monoxide, carbon dioxide, methylated amines (e.g., methylamine, dimethylamine, trimethylamine, etc.), methylated thiols, methyl halogens (e.g., bromomethane, chloromethane, iodomethane, dichloromethane, etc.), and cyanide.

As used herein, "$C_1$ metabolizing microorganism" or "$C_1$ metabolizing non-photosynthetic microorganism" refers to any microorganism having the ability to use a $C_1$ substrate as a source of energy or as its primary source of energy or as its sole source of energy and biomass, and may or may not use other carbon substrates (such as sugars and complex carbohydrates) for energy and biomass. For example, a $C_1$ metabolizing microorganism may oxidize a $C_1$ substrate, such as methane, natural gas, or methanol. $C_1$ metabolizing microorganisms include bacteria (such as Methanotrophs and Methylotrophs) and yeast. In certain embodiments, a $C_1$ metabolizing microorganism does not include a photosynthetic microorganism, such as algae. In certain embodiments, a $C_1$ metabolizing microorganism will be an "obligate $C_1$ metabolizing microorganism," meaning its primary source of energy are $C_1$ substrates. In further embodiments, a $C_1$ metabolizing microorganism (e.g., methanotroph) will be cultured in the presence of a $C_1$ substrate feedstock (i.e., using the $C_1$ substrate as the primary or sole source of energy).

As used herein, the term "methylotroph" or "methylotrophic bacteria" refers to any bacteria capable of oxidizing organic compounds that do not contain carbon-carbon bonds. In certain embodiments, a methylotrophic bacterium may be a methanotroph. For example, "methanotrophic bacteria" refers to any methylotrophic bacteria that have the ability to oxidize methane as it primary source of carbon and energy. Exemplary methanotrophic bacteria include *Methylomonas, Methylobacter, Methylococcus, Methylosinus, Methylocystis, Methylomicrobium*, or *Methanomonas*. In certain other embodiments, the methylotrophic bacterium is an "obligate methylotrophic bacterium," which refers to bacteria that are limited to the use of $C_1$ substrates for the generation of energy.

As used herein, the term "CO utilizing bacterium" refers to a bacterium that naturally possesses the ability to oxidize carbon monoxide (CO) as a source of carbon and energy. Carbon monoxide may be utilized from "synthesis gas" or "syngas", a mixture of carbon monoxide and hydrogen produced by gasification of any organic feedstock, such as coal, coal oil, natural gas, biomass, and waste organic matter. CO utilizing bacterium does not include bacteria that must be genetically modified for growth on CO as its carbon source.

As used herein, "natural gas" refers to naturally occurring gas mixtures that have formed in porous reservoirs and can be accessed by conventional processes (e.g., drilling) and are primarily made up of methane, but may also have other components such as carbon dioxide, nitrogen or hydrogen sulfide.

As used herein, "unconventional natural gas" refers to a naturally occurring gas mixture created in formations with low permeability that must be accessed by unconventional methods, such as hydraulic fracturing, horizontal drilling or directional drilling. Exemplary unconventional natural gas deposits include tight gas sands formed in sandstone or carbonate, coal bed methane formed in coal deposits and adsorbed in coal particles, shale gas formed in fine-grained shale rock and adsorbed in clay particles or held within small pores or microfractures, methane hydrates that are a crystalline combination of natural gas and water formed at low temperature and high pressure in places such as under the oceans and permafrost.

As used herein, "syngas" refers to a mixture of carbon monoxide (CO) and hydrogen ($H_2$). Syngas may also include $CO_2$, methane, and other gases in smaller quantities relative to CO and $H_2$.

As used herein, "methane" refers to the simplest alkane compound with the chemical formula $CH_4$. Methane is a colorless and odorless gas at room temperature and pressure. Sources of methane include natural sources, such as natural gas fields, "unconventional natural gas" sources (such as shale gas or coal bed methane, wherein content will vary depending on the source), and biological sources where it is synthesized by, for example, methanogenic microorganisms, and industrial or laboratory synthesis. Methane includes pure methane, substantially purified compositions, such as "pipeline quality natural gas" or "dry natural gas", which is 95-98% percent methane, and unpurified compositions, such as "wet natural gas", wherein other hydrocarbons have not yet been removed and methane comprises more than 60% of the composition.

As used herein, "nucleic acid molecule," also known as a polynucleotide, refers to a polymeric compound comprised of covalently linked subunits called nucleotides. Nucleic acid molecules include polyribonucleic acid (RNA), polydeoxyribonucleic acid (DNA), both of which may be single or double stranded. DNA includes cDNA, genomic DNA, synthetic DNA, semi-synthetic DNA, or the like.

As used herein, "transformation" refers to the transfer of a nucleic acid molecule (e.g., exogenous or heterologous nucleic acid molecule) into a host. The transformed host may carry the exogenous or heterologous nucleic acid molecule extra-chromosomally or the nucleic acid molecule may integrate into the chromosome. Integration into a host genome and self-replicating vectors generally result in genetically stable inheritance of the transformed nucleic acid molecule. Host cells containing the transformed nucleic acids are referred to as "recombinant" or "non-naturally occurring" or "genetically engineered" or "transformed" or "transgenic" cells (e.g., bacteria).

As used herein, the term "endogenous" or "native" refers to a gene, protein, compound or activity that is normally present in a host cell.

As used herein, "heterologous" nucleic acid molecule, construct or sequence refers to a nucleic acid molecule or portion of a nucleic acid molecule sequence that is not native to a host cell or is a nucleic acid molecule with an altered expression as compared to the native expression levels in similar conditions. For example, a heterologous control sequence (e.g., promoter, enhancer) may be used to regulate expression of a native gene or nucleic acid molecule in a way that is different from the way a native gene or nucleic acid molecule is normally expressed in nature or culture. In certain embodiments, heterologous nucleic acid molecules may not be endogenous to a host cell or host genome, but instead may have been added to a host cell by conjugation, transformation, transfection, electroporation, or the like, wherein the added molecule may integrate into the host genome or can exist as extra-chromosomal genetic material (e.g., as a plasmid or other self replicating vector). In addition, "heterologous" can refer to an enzyme, protein or other activity that is different or altered from that found in a host cell, or is not native to a host cell but instead is encoded by a nucleic acid molecule introduced into the host cell. The term "homologous" or "homolog" refers to a molecule or activity found in or derived from a host cell, species or strain. For example, a heterologous nucleic acid molecule may be homologous to a native host cell gene, but may have an altered expression level or have a different sequence or both.

In certain embodiments, more than one heterologous nucleic acid molecules can be introduced into a host cell as separate nucleic acid molecules, as a polycistronic nucleic acid molecule, as a single nucleic acid molecule encoding a fusion protein, or any combination thereof, and still be considered as more than one heterologous nucleic acid. For example, as disclosed herein, a $C_1$ metabolizing microorganism can be modified to express two or more heterologous or exogenous nucleic acid molecules encoding desired fatty acid biosynthesis pathway components (e.g., thioesterase, fatty acyl-CoA reductase, alcohol dehydrogenase). When two or more exogenous nucleic acid molecules encoding fatty acid biosynthesis pathway components are introduced into a host $C_1$ metabolizing microorganism, it is understood that the two more exogenous nucleic acid molecules can be introduced as a single nucleic acid molecule, for example, on a single vector, on separate vectors, can be integrated into the host chromosome at a single site or multiple sites, and still be considered two or more exogenous nucleic acid molecules. Thus, the number of referenced heterologous nucleic acid molecules or protein activities refers to the number of encoding nucleic acid molecules or the number of protein activities, not the number of separate nucleic acid molecules introduced into a host cell.

The term "chimeric" refers to any nucleic acid molecule or protein that is not endogenous and comprises sequences joined or linked together that are not normally found joined or linked together in nature. For example, a chimeric nucleic acid molecule may comprise regulatory sequences and coding sequences that are derived from different sources, or regulatory sequences and coding sequences that are derived from the same source but arranged in a manner different than that found in nature.

The "percent identity" between two or more nucleic acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:N.Y. (1975), pp. 71-'7'7; Lewin, Genes IV, Oxford University Press, NY and Cell Press, Cambridge, Mass. (1990), p. 8).

"Inhibit" or "inhibited," as used herein, refers to an alteration, reduction, down regulation or abrogation, directly or indirectly, in the expression of a target gene or in the activity of a target molecule (e.g., thioesterase, acyl-CoA synthetase, alcohol dehydrogenase) relative to a control, endogenous or reference molecule, wherein the alteration, reduction, down regulation or abrogation is statistically, biologically, industrially, or clinically significant.

As used herein, the term "derivative" refers to a modification of a compound by chemical or biological means, with or without an enzyme, which modified compound is structurally similar to a parent compound and (actually or theoretically) derivable from that parent compound. A derivative may have different chemical, biological or physical properties of the parent compound, such as being more hydrophilic or having altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). Other exemplary derivatizations include glycosylation, alkylation, acylation, acetylation, ubiquitination, esterification, and amidation. As used herein, "fatty acid derivatives" include intermediates and products of the fatty acid biosynthesis pathway found in cells, such as fatty acyl carrier proteins, activated fatty acids (e.g., acyl or CoA containing), fatty aldehydes, fatty alcohols, fatty ester wax, hydroxy fatty acids, dicarboxylic acids, branched fatty acids, or the like.

The term "derivative" also refers to all solvates, for example, hydrates or adducts (e.g., adducts with alcohols), active metabolites, and salts of the parent compound. The type of salt that may be prepared depends on the nature of the moieties within the compound. For example, acidic groups such as carboxylic acid groups can form alkali metal salts or alkaline earth metal salts (e.g., sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts, for example, with inorganic acids such as hydrochloric acid, sulfuric acid or phosphoric acid, or with organic carboxylic acids and sulfonic acids such as acetic acid, citric acid, lactic acid, benzoic acid, maleic acid, fumaric acid, tartaric acid, methanesulfonic acid or p-toluenesulfonic acid. Compounds that simultaneously contain a basic group and an acidic group, for example, a carboxyl group in addition to basic nitrogen atoms, can be present as zwitterions. Salts can be obtained by customary methods known to those skilled in the art, for example, by combining a compound with an inorganic or organic acid or base in a solvent or diluent, or from other salts by cation exchange or anion exchange.

Compositions and Methods for Making Fatty Acid Derivatives

The $C_1$ metabolizing microorganisms used to produce fatty acid derivatives can be recombinantly modified to include nucleic acid sequences that express or over-express polypeptides of interest. For example, a $C_1$ metabolizing microorganism can be modified to increase the production of acyl-CoA and reduce the catabolism of fatty acid derivatives and intermediates in the fatty acid biosynthetic pathway, such as acyl-CoA, or to reduce feedback inhibition at specific points in the fatty acid biosynthetic pathway. In addition to modifying the genes described herein, additional cellular resources can be diverted to over-produce fatty acids, for example, the lactate, succinate or acetate pathways can be attenuated, and acetyl-CoA carboxylase (acc) can be over-expressed. The modifications to a $C_1$ metabolizing microorganisms described herein can be through genomic alterations, addition of recombinant expression systems, or a combination thereof.

The fatty acid biosynthetic pathways involved are illustrated in FIGS. 1 to 6. Different steps in the pathway are catalyzed by different enzymes and each step is a potential place for over-expression of the gene to produce more enzyme and thus drive the production of more fatty acids and fatty acid derivatives. Nucleic acid molecules encoding enzymes required for the pathway may also be recombinantly added to a $C_1$ metabolizing microorganism lacking such enzymes. Finally, steps that would compete with the pathway leading to production of fatty acids and fatty acid derivatives can be attenuated or blocked in order to increase the production of the desired products.

Fatty acid synthases (FASs) are a group of enzymes that catalyze the initiation and elongation of acyl chains (Marrakchi et al., *Biochemical Society* 30:1050, 2002). The acyl carrier protein (ACP) along with the enzymes in the FAS pathway control the length, degree of saturation, and branching of the fatty acids produced. The steps in this pathway are catalyzed by enzymes of the fatty acid biosynthesis (fab) and acetyl-CoA carboxylase (acc) gene families. Depending upon the desired product, one or more of these genes can be attenuated, expressed or over-expressed (see FIGS. 1-6 for a depiction of the enzymatic activity of each enzyme and its enzyme classification number).

The fatty acid biosynthetic pathway in the production host uses the precursors acetyl-CoA and malonyl-CoA (see, e.g., FIG. 1). The steps in this pathway are catalyzed by enzymes of the fatty acid biosynthesis (fab) and acetyl-CoA carboxylase (acc) gene families. This pathway is described in Heath et al., *Prog. Lipid Res.* 40:467, 2001.

Acetyl-CoA is carboxylated by acetyl-CoA carboxylase (Acc, a multisubunit enzyme encoded by four separate genes, accABCD), to form malonyl-CoA. The malonate group is transferred to ACP by malonyl-CoA:ACP transacylase (FabD) to form malonyl-ACP. A condensation reaction then occurs, where malonyl-ACP merges with acetyl-CoA, resulting in β-ketoacyl-ACP. β-ketoacyl-ACP synthase III (FabH) initiates the FAS cycle, while β-ketoacyl-ACP synthase I (FabB) and β-ketoacyl-ACP synthase II (FabF) are involved in subsequent cycles.

Next, a cycle of steps is repeated until a saturated fatty acid of the appropriate length is made. First, the β-ketoacyl-ACP is reduced by NADPH to form β-hydroxyacyl-ACP. This step is catalyzed by β-ketoacyl-ACP reductase (FabG). β-hydroxyacyl-ACP is then dehydrated to form trans-2-enoyl-ACP. β-hydroxyacyl-ACP dehydratase/isomerase (FabA) or β-hydroxyacyl-ACP dehydratase (FabZ) catalyzes this step. NADPH-dependent trans-2-enoyl-ACP reductase I, II, or III (FabI, FabK, and FabL, respectively) reduces trans-2-enoyl-ACP to form acyl-ACP. Subsequent cycles are started by the condensation of malonyl-ACP with acyl-ACP by β-ketoacyl-ACP synthase I or β-ketoacyl-ACP synthase II (FabB and FabF, respectively).

$C_1$ metabolizing microorganisms as described herein may be engineered to overproduce acetyl-CoA and malonyl-CoA. Several different modifications can be made, either in combination or individually, to a $C_1$ metabolizing microorganism to obtain increased acetyl-CoA/malonyl-CoA/fatty acid and fatty acid derivative production.

For example, to increase acetyl-CoA production, one or more of the following genes could be expressed in a $C_1$ metabolizing microorganism: pdh, panK, aceEF (encoding the E1p dehydrogenase component and the E2p dihydrolipoamide acyltransferase component of the pyruvate and 2-oxoglutarate dehydrogenase complexes), fabH, fabD, fabG, acpP, or fabF. In other examples, additional DNA sequence encoding fatty-acyl-CoA reductases and aldehyde decarbonylases could be expressed in a $C_1$ metabolizing microorganism. It is well known in the art that a plasmid containing one or more of the aforementioned genes, all under the control of a constitutive, or otherwise controllable promoter, can be constructed. Exemplary GenBank accession numbers for these genes are pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179).

Additionally, the expression levels of fadE, gpsA, ldhA, pflb, adhE, pta, poxB, ackA, or ackB can be reduced, inhibited or knocked-out in the engineered microorganism by transformation with conditionally replicative or non-replicative plasmids containing null or deletion mutations of the corresponding genes, or by substituting promoter or enhancer sequences. Exemplary GenBank accession numbers for these genes are fadE (AAC73325), gspA (AAC76632), ldhA (AAC74462), pflb (AAC73989), adhE (AAC74323), pta (AAC75357), poxB (AAC73958), ackA (AAC75356), and ackB (BAB81430). The resulting engineered $C_1$ metabolizing microorganisms will have increased acetyl-CoA production levels when grown in an appropriate environment, such as with a $C_1$ substrate feedstock.

Moreover, malonyl-CoA overproduction can be affected by engineering the $C_1$ metabolizing microorganisms as described herein with accABCD (e.g., accession number AAC73296, EC 6.4.1.2) included in the plasmid synthesized de novo. Fatty acid overproduction can be achieved by further including a nucleic acid molecule encoding lipase (e.g., Genbank Accession Nos. CAA89087, CAA98876) in the plasmid synthesized de novo.

As a result, in some examples, acetyl-CoA carboxylase is over-expressed to increase the intracellular concentration thereof by at least about 2-fold, preferably at least about 5-fold, or more preferably at least about 10-fold, relative to native expression levels.

In some embodiments, the plsB (e.g., Genbank Accession No. AAC77011) D311E mutation can be used to increase the amount of available acyl-CoA. In further embodiments, over-expression of a sfa gene (suppressor of FabA, e.g., Genbank Accession No. AAN79592) can be included in a $C_1$ metabolizing microorganism to increase production of monounsaturated fatty acids (Rock et al., *J. Bacteriology* 178:5382, 1996).

As described herein, acetyl-CoA and malonyl-CoA are processed in several steps to form acyl-ACP chains. The enzyme sn-glycerol-3-phosphate acyltransferase (PlsB) catalyzes the transfer of an acyl group from acyl-ACP or acyl-CoA to the sn-1 position of glycerol-3-phosphate. Thus, PlsB is a key regulatory enzyme in phospholipid synthesis, which is part of the fatty acid pathway. Inhibiting PlsB leads to an increase in the levels of long chain acyl-ACP, which feedback will inhibit early steps in the pathway (e.g., accABCD, fabH, and fabI). Uncoupling of this regulation, for example, by thioesterase overexpression leads to increased fatty acid production. The tes and fat gene families express thioesterase. FabI is also inhibited in vitro by long-chain acyl-CoA.

To engineer a $C_1$ metabolizing microorganism for the production of a homogeneous or mixed population of fatty acid derivatives, one or more endogenous genes can be attenuated, inhibited or functionally deleted and, as a result, one or more thioesterases can be expressed. For example, $C_{10}$ fatty acid derivatives can be produced by attenuating thioesterase $C_{18}$ (e.g., Genbank Accession Nos. AAC73596 and P0ADA1), which uses $C_{18:1}$-ACP, and at the same time expressing thioesterase $C_{10}$ (e.g., Genbank Accession No. Q39513), which uses $C_{10}$-ACP. This results in a relatively homogeneous population of fatty acid derivatives that have a carbon chain length of 10. In another example, $C_{14}$ fatty acid derivatives can be produced by attenuating endogenous thioesterases that produce non-$C_{14}$ fatty acids and expressing the thioesterase accession number Q39473 (which uses $C_{14}$-ACP). In yet another example, $C_{12}$ fatty acid derivatives can be produced by expressing thioesterases that use $C_{12}$-ACP (for example, Genbank Accession No. Q41635) and attenuating thioesterases that produce non-$C_{12}$ fatty acids. Acetyl-CoA, malonyl-CoA, and fatty acid overproduction can be verified using methods known in the art, for example by using radioactive precursors, HPLC, and GC-MS subsequent to cell lysis. Non-limiting examples of thioesterases useful in the claimed methods and $C_1$ metabolizing microorganisms of this disclosure are listed in Table 1 of U.S. Pat. No. 8,283,143, which table is hereby incorporated by reference in its entirety.

Acyl-CoA synthase (ACS) esterifies free fatty acids to acyl-CoA by a two-step mechanism. The free fatty acid first is converted to an acyl-AMP intermediate (an adenylate) through the pyrophosphorolysis of ATP. The activated carbonyl carbon of the adenylate is then coupled to the thiol group of CoA, releasing AMP and the acyl-CoA final product. See Shockey et al., *Plant. Physiol.* 129:1710, 2002.

The *E. coli* ACS enzyme FadD and the fatty acid transport protein FadL are essential components of a fatty acid uptake system. FadL mediates transport of fatty acids into the bacterial cell, and FadD mediates formation of acyl-CoA esters. When no other carbon source is available, exogenous fatty acids are taken up by bacteria and converted to acyl-CoA esters, which bind to the transcription factor FadR and derepress the expression of the fad genes that encode proteins responsible for fatty acid transport (FadL), activation (FadD), and β-oxidation (FadA, FadB, FadE, and FadH). When alternative sources of carbon are available bacteria synthesize fatty acids as acyl-ACPs, which are used for phospholipid synthesis, but are not substrates for β-oxidation. Thus, acyl-CoA and acyl-ACP are both independent sources of fatty acids that will result in different endproducts. See Caviglia et al., *J. Biol. Chem.* 279:1163, 2004.

$C_1$ metabolizing microorganisms can be engineered using nucleic acid molecules encoding known polypeptides to produce fatty acids of various lengths, which can then be converted to acyl-CoA and ultimately to fatty acid derivatives, such as fatty alcohol. One method of making fatty acid derivatives involves increasing the expression, or expressing more active forms, of one or more acyl-CoA synthase peptides (EC 6.2.1.-). A list of acyl-CoA synthases that can be expressed to produce acyl-CoA and fatty acid derivatives is shown in Table 2 of U.S. Pat. No. 8,283,143, which table is hereby incorporated by reference in its entirety. These acyl-CoA synthases can be used to improve any pathway that uses fatty-acyl-CoAs as substrates.

Acyl-CoA is reduced to a fatty aldehyde by NADH-dependent acyl-CoA reductase (e.g., Acr1). The fatty aldehyde is then reduced to a fatty alcohol by NADPH-dependent alcohol dehydrogenase (e.g., YqhD). Alternatively, fatty alcohol forming acyl-CoA reductase (FAR) catalyzes the reduction of an acyl-CoA into a fatty alcohol and CoASH. FAR uses NADH or NADPH as a cofactor in this four-electron reduction. Although the alcohol-generating FAR reactions proceed through an aldehyde intermediate, a free aldehyde is not released. Thus, alcohol-forming FARs are distinct from those enzymes that carry out two-electron reductions of acyl-CoA and yield free fatty aldehyde as a product. (See Cheng and Russell, *J. Biol. Chem.*, 279:37789, 2004; Metz et al., *Plant Physiol.* 122:635, 2000).

$C_1$ metabolizing microorganisms can be engineered using known polypeptides to produce fatty alcohols from acyl-CoA. One method of making fatty alcohols involves increasing the expression of, or expressing more active forms of, fatty alcohol forming acyl-CoA reductases (encoded by a gene such as acr1 from FAR, EC 1.2.1.50/1.1.1) or acyl-CoA reductases (EC 1.2.1.50) and alcohol dehydrogenase (EC 1.1.1.1). Exemplary GenBank Accession Numbers are listed in FIG. 1 of U.S. Pat. No. 8,283,143, which figure is hereby incorporated by reference in its entirety.

Fatty alcohols can be described as hydrocarbon-based surfactants. For surfactant production, a $C_1$ metabolizing microorganism is modified so that it produces a surfactant from a $C_1$ substrate feedstock. Such a $C_1$ metabolizing microorganism includes a first exogenous nucleic acid molecule encoding a protein capable of converting a fatty acid to a fatty aldehyde and a second exogenous nucleic acid molecule encoding a protein capable of converting a fatty aldehyde to an alcohol. In some examples, a first exogenous nucleic acid molecule encodes a fatty acid reductase (FAR). In one embodiment, a second exogenous nucleic acid molecule encodes mammalian microsomal aldehyde reductase or long-chain aldehyde dehydrogenase. In a further example, first and second exogenous nucleic acid molecules are from *Arthrobacter* AK 19, *Rhodotorula glutinins*, *Acinetobacter* sp. M-1, or *Candida lipolytica*. In one embodiment, first and second heterologous nucleic acid molecules are from a multienzyme complex from *Acinetobacter* sp. M-1 or *Candida lipolytica*.

Additional sources of heterologous nucleic acid molecules encoding fatty acid to long chain alcohol converting proteins that can be used in surfactant production include *Mortierella alpina* (ATCC 32222), *Cryptococcus curvatus*, (also referred to as *Apiotricum curvatum*), *Akanivorax jadensis* (T9T=DSM 12718=ATCC 700854), *Acinetobacter* sp. HO1-N (ATCC 14987) and *Rhodococcus opacus* (PD630 DSMZ 44193).

In one example, a fatty acid derivative is a saturated or unsaturated surfactant product having a carbon chain length of about 8 to about 24 carbon atoms, about 8 to about 18 carbon atoms, about 8 to about 14 carbon atoms, about 10 to about 18 carbon atoms, or about 12 to about 16 carbon atoms. In another example, the surfactant product has a carbon chain length of about 10 to about 14 carbon atoms, or about 12 to about 14 carbon atoms.

Appropriate $C_1$ metabolizing microorganisms for producing surfactants can be either eukaryotic or prokaryotic microorganisms. $C_1$ metabolizing microorganisms that demonstrate an innate ability to synthesize high levels of surfactant precursors from $C_1$ feedstock in the form of fatty acid derivatives, such as methanogens engineered to express acetyl CoA carboxylase are used.

Production hosts can be engineered using known polypeptides to produce fatty esters of various lengths. One method of making fatty esters includes increasing the expression of, or expressing more active forms of, one or more alcohol O-acetyltransferase peptides (EC 2.3.1.84). These peptides catalyze the acetylation of an alcohol by converting an acetyl-CoA and an alcohol to a CoA and an ester. In some examples, the alcohol O-acetyltransferase peptides can be expressed in conjunction with selected thioesterase peptides, FAS peptides, and fatty alcohol forming peptides, thus allowing the carbon chain length, saturation, and degree of branching to be controlled. In some cases, a bkd operon can be coexpressed to enable branched fatty acid precursors to be produced.

As used herein, alcohol O-acetyltransferase peptides include peptides in enzyme classification number EC 2.3.1.84, as well as any other peptide capable of catalyzing the conversion of acetyl-CoA and an alcohol to form a CoA and an ester. Additionally, one of ordinary skill in the art will appreciate that alcohol O-acetyltransferase peptides will catalyze other reactions.

For example, some alcohol O-acetyltransferase peptides will accept other substrates in addition to fatty alcohols or acetyl-CoA thioester, such as other alcohols and other acyl-CoA thioesters. Such non-specific or divergent-specificity alcohol O-acetyltransferase peptides are, therefore, also included. Alcohol O-acetyltransferase peptide sequences are publicly available and exemplary GenBank Accession Numbers are listed in FIG. 1 of U.S. Pat. No. 8,283,143, which figure is hereby incorporated by reference in its entirety. Assays for characterizing the activity of particular alcohol O-acetyltransferase peptides are well known in the art. O-acyltransferases can be engineered to have new activities and specificities for the donor acyl group or acceptor alcohol moiety. Engineered enzymes can be generated through well-documented rational and evolutionary approaches.

Fatty esters are synthesized by acyl-CoA:fatty alcohol acyltransferase (e.g., ester synthase), which conjugate a long chain fatty alcohol to a fatty acyl-CoA via an ester linkage. Ester synthases and encoding genes are known from the jojoba plant and the bacterium *Acinetobacter* sp. ADP1 (formerly *Acinetobacter calcoaceticus* ADP1). The bacterial ester synthase is a bifunctional enzyme, exhibiting ester synthase activity and the ability to form triacylglycerols from diacylglycerol substrates and fatty acyl-CoAs (acyl-CoA:diglycerol acyltransferase (DGAT) activity). The gene wax/dgat encodes both ester synthase and DGAT. See Cheng et al., *J. Biol. Chem.* 279:37798, 2004; Kalscheuer and Steinbuchel, *J. Biol. Chem.* 278:8075, 2003. Ester synthases may also be used to produce certain fatty esters.

The production of fatty esters, including waxes, from acyl-CoA and alcohols, can be engineered using known polypeptides. One method of making fatty esters includes increasing the expression of, or expressing more active forms of, one or more ester synthases (EC 2.3.1.20, 2.3.1.75). Ester synthase peptide sequences are publicly available and exemplary GenBank Accession Numbers are listed in FIG. 1 of U.S. Pat. No. 8,283,143, which figure is hereby incorporated by reference in its entirety. Methods to identify ester synthase activity are provided in U.S. Pat. No. 7,118,896.

In particular examples, if a desired product is a fatty acid ester wax, a $C_1$ metabolizing microorganism is modified so that it produces an ester. Such a $C_1$ metabolizing microorganism includes an exogenous nucleic acid molecule encoding an ester synthase that is expressed so as to confer upon a $C_1$ metabolizing microorganism the ability to synthesize a saturated, unsaturated, or branched fatty ester from a $C_1$ substrate feedstock. In some embodiments, a $C_1$ metabolizing microorganism can also express nucleic acid molecules encoding the following exemplary proteins: fatty acid elongases, acyl-CoA reductases, acyltransferases, ester synthases, fatty acyl transferases, diacylglycerol acyltransferases, acyl-coA wax alcohol acyltransferases, or any combination thereof. In an alternate embodiment, $C_1$ metabolizing microorganisms comprises a nucleic acid molecule encoding a bifunctional ester synthase/acyl-CoA:diacylglycerol acyltransferase. For example, the bifunctional ester synthase/acyl-CoA:diacylglycerol acyltransferase can be selected from the multienzyme complexes from *Simmondsia chinensis*, *Acinetobacter* sp. ADP1 (formerly *Acinetobacter calcoaceticus* ADP1), *Alcanivorax borkumensis*, *Pseudomonas aeruginosa*, *Fundibacter jadensis*, *Arabidopsis thaliana*, or *Alcaligenes eutrophus* (later renamed *Ralstonia eutropha*). In one embodiment, fatty acid elongases, acyl-CoA reductases or wax synthases are from a multienzyme complex from *Ralstonia eutropha* or other organisms known in the literature to produce esters, such as wax or fatty esters.

Additional sources of heterologous nucleic acid molecules encoding ester synthesis proteins useful in fatty ester production include *Mortierella alpina* (e.g., ATCC 32222), *Cryptococcus curvatus* (also referred to as *Apiotricum curvatum*), *Alcanivorax jadensis* (for example, T9T=DSM 12718=ATCC 700854), *Acinetobacter* sp. HO1-N (e.g., ATCC 14987), and *Rhodococcus opacus* (e.g., PD630, DSMZ 44193). In one example, the ester synthase from *Acinetobacter* sp. ADP1 at locus AA017391 (described in Kalscheuer and Steinbuchel, *J. Biol. Chem.* 278:8075, 2003) is used. In another example, an ester synthase from *Simmondsia chinensis* at locus AAD38041 is used.

Optionally, an ester exporter such as a member of the FATP family can be used to facilitate the release of esters into the extracellular environment. A non-limiting example of an ester exporter that can be used is fatty acid (long chain) transport protein CG7400-PA, isoform A, from *Drosophila melanogaster*, at locus NP 524723.

Transport proteins export fatty acid derivatives out of a $C_1$ metabolizing microorganism. Many transport and efflux proteins serve to excrete a large variety of compounds, and can naturally be modified to be selective for particular types of fatty acid derivatives. Non-limiting examples of suitable transport proteins are ATP-Binding Cassette (ABC) transport proteins, efflux proteins, and fatty acid transporter proteins (FATP). Additional non-limiting examples of suitable transport proteins include the ABC transport proteins from organisms such as *Caenorhabditis elegans, Arabidopsis thalania, Alkaligenes eutrophus, Rhodococcus erythropolis*. Exemplary ABC transport proteins which could be used are CER5, AtMRP5, AmiS2, or AtPGP1. In a preferred embodiment, an ABC transport protein is CER5 (e.g., AY734542). Vectors containing genes that express suitable transport proteins can be inserted into the protein production host to increase the release of fatty acid derivatives.

$C_1$ metabolizing microorganisms can also be chosen for their endogenous ability to release fatty acid derivatives. The efficiency of product production and release into the fermentation broth can be expressed as a ratio of intracellular product to extracellular product. In some examples, the ratio can be about 5:1, 4:1, 3:1, 2:1, 1:1, 1:2, 1:3, 1:4, or 1.5.

Fatty acid derivatives with particular branch points, levels of saturation, carbon chain length, and ester characteristics can be produced as desired. $C_1$ metabolizing microorganisms that naturally produce particular derivatives can be chosen as the initial host cell. Alternatively, genes that express enzymes that will produce particular fatty acid derivatives can be inserted into a $C_1$ metabolizing microorganism as described herein.

In some examples, the expression of exogenous FAS genes originating from different species or engineered variants can be introduced into a $C_1$ metabolizing microorganism to allow for the biosynthesis of fatty acids that are structurally different (in length, branching, degree of unsaturation, etc.) from those of the native host cell. These heterologous gene products can also be chosen or engineered to be unaffected by the natural regulatory mechanisms in the host cell, and therefore allow for control of the production of the desired commercial product. For example, FAS enzymes from *Bacillus subtilis, Saccharomyces cerevisiae, Streptomyces* spp., *Ralstonia, Rhodococcus, Corynebacteria, Brevibacteria, Mycobacteria*, oleaginous yeast, or the like can be expressed in a $C_1$ metabolizing microorganism. The expression of such exogenous enzymes will alter the structure of the fatty acid produced and ultimately the fatty acid derivative.

When a $C_1$ metabolizing microorganism is engineered to produce a fatty acid with a specific level of unsaturation, branching, or carbon chain length, the resulting engineered fatty acid can be used in the production of fatty acid derivatives. Fatty acid derivatives generated from such $C_1$ metabolizing microorganisms can display the characteristics of the engineered fatty acid.

For example, a production host can be engineered to make branched, short chain fatty acids, which may then be used by the production host to produce branched, short chain fatty alcohols. Similarly, a hydrocarbon can be produced by engineering a production host to produce a fatty acid having a defined level of branching, unsaturation, or carbon chain length; thus, producing a homogeneous hydrocarbon population. Additional steps can be employed to improve the homogeneity of the resulting product. For example, when an unsaturated alcohol, fatty ester, or hydrocarbon is desired, a $C_1$ metabolizing microorganism can be engineered to produce low levels of saturated fatty acids and in addition can be modified to express an additional desaturase to lessen or reduce the production of a saturated product.

Fatty acids are a key intermediate in the production of fatty acid derivatives. Fatty acid derivatives can be produced to contain branch points, cyclic moieties, and combinations thereof, by using branched or cyclic fatty acids to make the fatty acid derivatives.

For example, $C_1$ metabolizing microorganisms may naturally produce straight chain fatty acids. To engineer $C_1$ metabolizing microorganisms to produce branched chain fatty acids, several genes that provide branched precursors (e.g., bkd operon) can be introduced into a $C_1$ metabolizing microorganism (e.g., methanogen) and expressed to allow initiation of fatty acid biosynthesis from branched precursors (e.g., fabH). The bkd, ilv, icm, and fab gene families may be expressed or over-expressed to produce branched chain fatty acid derivatives. Similarly, to produce cyclic fatty acids, genes that provide cyclic precursors can be introduced into the production host and expressed to allow initiation of fatty acid biosynthesis from cyclic precursors. The ans, chc, and plm gene families may be expressed or over-expressed to produce cyclic fatty acids. Non-limiting examples of genes in these gene families that may be used in the present methods and $C_1$ metabolizing microorganisms of this disclosure are listed in U.S. Pat. No. 8,283,143 (FIG. 1, which figure is herein incorporated by reference).

Additionally, the production host can be engineered to express genes encoding proteins for the elongation of branched fatty acids (e.g., ACP, FabF, etc.) or to delete or attenuate the corresponding genes that normally lead to straight chain fatty acids. In this regard, endogenous genes that would compete with the introduced genes (e.g., fabH, fabF) are deleted, inhibited or attenuated.

The branched acyl-CoA (e.g., 2-methyl-butyryl-CoA, isovaleryl-CoA, isobutyryl-CoA, etc.) are the precursors of branched fatty acids. In most microorganisms containing branched fatty acids, the branched fatty acids are synthesized in two steps from branched amino acids (e.g., isoleucine, leucine, and valine) (Kadena, *Microbial. Rev.* 55:288, 1991). A $C_1$ metabolizing microorganism can be engineered to express or over-express one or more of the enzymes involved in these two steps to produce branched fatty acid derivatives, or to over-produce branched fatty acid derivatives. For example, a $C_1$ metabolizing microorganism may have an endogenous enzyme that can accomplish one step leading to branched fatty acid derivative; therefore, only genes encoding enzymes involved in the second step need to be introduced recombinantly.

The first step in forming branched fatty acid derivatives is the production of the corresponding α-keto acids by a branched-chain amino acid aminotransferase. $C_1$ metabolizing microorganisms, such as methanotrophs, may endogenously include genes encoding such enzymes or such genes may be recombinantly introduced. In some $C_1$ metabolizing microorganisms, a heterologous branched-chain amino acid aminotransferase may not be expressed. Hence, in certain embodiments, IlvE from *E. coli* or any other branched-chain amino acid aminotransferase (e.g., IlvE from *Lactococcus lactis* (GenBank accession AAF34406), IlvE from *Pseudomonas putida* (GenBank accession NP 745648), or IlvE from *Streptomyces coelicolor* (GenBank accession NP_629657)) can be introduced into $C_1$ metabolizing microorganisms of this disclosure. If the aminotransferase reaction is rate limiting in branched fatty acid biosynthesis in the chosen $C_1$ metabolizing microorganism, then an aminotransferase can be over-expressed.

The second step is the oxidative decarboxylation of the α-ketoacids to the corresponding branched-chain acyl-CoA. This reaction can be catalyzed by a branched-chain α-keto acid dehydrogenase complex (bkd; EC 1.2.4.4.) (Denoya et al., *J. Bacteriol.* 177:3504, 1995), which includes E1α/β (decarboxylase), E2 (dihydrolipoyl transacylase) and E3 (dihydrolipoyl dehydrogenase) subunits. These branched-chain α-keto acid dehydrogenase complexes are similar to pyruvate and α-ketoglutarate dehydrogenase complexes. Every microorganism that possesses branched fatty acids or grows on branched-chain amino acids can be used as a source to isolate bkd genes for expression in $C_1$ metabolizing microorganisms, such as methanotrophs. Furthermore, if the $C_1$ metabolizing microorganism has an E3 component as part of its pyruvate dehydrogenase complex (lpd, EC 1.8.1.4), then it may be sufficient to only express the E1α/β and E2 bkd genes.

In another example, isobutyryl-CoA can be made in a $C_1$ metabolizing microorganism, for example, in a methanotroph, through the coexpression of a crotonyl-CoA reductase (Ccr, EC 1.6.5.5, 1.1.1.1) and isobutyryl-CoA mutase (large subunit IcmA, EC 5.4.99.2; small subunit IcmB, EC 5.4.99.2) (Han and Reynolds, *J. Bacteriol.* 179:5157, 1997). Crotonyl-CoA is an intermediate in fatty acid biosynthesis in *E. coli* and other microorganisms.

In addition to expression of the bkd genes, the initiation of brFA biosynthesis utilizes β-ketoacyl-acyl-carrier-protein synthase III (FabH, EC 2.3.1.41) with specificity for branched chain acyl-CoAs (Li et al., *J. Bacteriol.* 187:3795, 2005). A fabH gene that is involved in fatty acid biosynthesis of any branched fatty acid-containing microorganism can be expressed in a $C_1$ metabolizing microorganism of this disclosure. The Bkd and FabH enzymes from production hosts that do not naturally make branched fatty acids or derivatives thereof may not support branched fatty acid production; therefore, Bkd and FabH can be expressed recombinantly. Vectors containing the bkd and fabH genes can be inserted into such a $C_1$ metabolizing microorganism. Similarly, the endogenous level of Bkd and FabH production may not be sufficient to produce branched fatty acid derivatives, so in certain embodiments they are over-expressed. Additionally, other components of the fatty acid biosynthesis pathway can be expressed or over-expressed, such as acyl carrier proteins (ACPs) and β-ketoacyl-acyl-carrier-protein synthase II (fabF, EC 2.3.1.41). In addition to expressing these genes, some genes in the endogenous fatty acid biosynthesis pathway may be attenuated in the $C_1$ metabolizing microorganisms of this disclosure. Genes encoding enzymes that would compete for substrate with the enzymes of the pathway that result in brFA production may be attenuated or inhibited to increase branched fatty acid derivative production.

As mentioned above, branched chain alcohols can be produced through the combination of expressing genes that support branched fatty acid synthesis and alcohol synthesis. For example, when an alcohol reductase, such as Acr1 from *Acinetobacter* baylyi ADP1, is coexpressed with a bkd operon, $C_1$ metabolizing microorganisms of this disclosure can synthesize isopentanol, isobutanol or 2-methyl butanol. Similarly, when Acr1 is coexpressed with ccr/icm genes, $C_1$ metabolizing microorganisms of this disclosure can synthesize isobutanol.

To convert a $C_1$ metabolizing microorganisms of this disclosure, such as a methanotroph, into an organism capable of synthesizing w-cyclic fatty acids (cyFA), a gene that provides the cyclic precursor cyclohexylcarbonyl-CoA (CHC-CoA) (Cropp et al., *Nature Biotech.* 18:980, 2000) is introduced and expressed in the $C_1$ metabolizing microorganisms of this disclosure.

Non-limiting examples of genes that provide CHC-CoA include ansJ, ansK, ansL, chcA and ansM from the ansatrienin gene cluster of *Streptomyces collinus* (Chen et al., *Eur. J. Biochem.* 261:98, 1999) or plmJ, plmK, plmL, chcA and plmM from the phoslactomycin B gene cluster of *Streptomyces* sp. HK803 (Palaniappan et al., *J. Biol. Chem.* 278:35552, 2003) together with the chcB gene (Patton et al., *Biochem.* 39:7595, 2000) from *S. collinus, S. avermitilis* or *S. coelicolor*. The FabH, ACP and fabF genes can be expressed to allow initiation and elongation of co-cyclic fatty acids. Alternatively, the homologous genes can be isolated from microorganisms that make cyFA and expressed in $C_1$ metabolizing microorganisms of this disclosure.

The genes fabH, acp and fabF are sufficient to allow initiation and elongation of w-cyclic fatty acids because they can have broad substrate specificity. If the coexpression of any of these genes with the ansJKLM/chcAB or pm1JKLM/chcAB genes does not yield cyFA, then fabH, acp or fabF homologs from microorganisms that make cyFAs can be isolated (e.g., by using degenerate PCR primers or heterologous DNA sequence probes) and co-expressed.

Fatty acids are a key intermediate in the production of fatty acid derivatives. The degree of saturation in fatty acid derivatives can be controlled by regulating the degree of saturation of the fatty acid intermediates. The sfa, gns, and fab families of genes can be expressed or over-expressed to control the saturation of fatty acids. Non-limiting examples of genes in these gene families that may be used in the present methods, and with $C_1$ metabolizing microorganisms of this disclosure, are listed in FIG. 1 of U.S. Pat. No. 8,283,143, which figure is herein incorporated by reference in its entirety.

$C_1$ metabolizing microorganisms of this disclosure can be engineered to produce unsaturated fatty acid derivatives by engineering the $C_1$ metabolizing microorganisms (e.g., methanotrophs) to over-express fabB, or by growing the $C_1$ metabolizing microorganism at low temperatures (e.g., less than 37° C.). In *E. coli*, FabB has preference to cisΔ³decenoyl-ACP and results in unsaturated fatty acid production. Over-expression of FabB results in the production of a significant percentage of unsaturated fatty acids (de Mendoza et al., *J. Biol. Chem.* 258:2098, 1983). A nucleic acid molecule encoding a fabB may be inserted into and expressed in $C_1$ metabolizing microorganisms (e.g., methanotrophs) not naturally having the gene. These unsaturated fatty acids can then be used as intermediates in $C_1$ metabolizing microorganisms that are engineered to produce fatty acid derivatives, such as fatty alcohols, fatty esters, waxes, hydroxy fatty acids, dicarboxylic acids, or the like. Alternatively, a repressor of fatty acid biosynthesis, for example, fabR can be inhibited or deleted in $C_1$ metabolizing microorganisms (e.g., methanotrophs), which may also result in increased unsaturated fatty acid production as is seen in *E. coli* (Zhang et al., *J. Biol. Chem.* 277:15558, 2002). Further increase in unsaturated fatty acids may be achieved, for example, by over-expression of fabM (trans-2, cis-3-decenoyl-ACP isomerase) and controlled expression of fabK (trans-2-enoyl-ACP reductase II) from *Streptococcus pneumoniae* (Marrakchi et al., *J. Biol. Chem.* 277:44809, 2002), while deleting fabI (trans-2-enoyl-ACP reductase). Additionally, to increase the percentage of unsaturated fatty esters, a $C_1$ metabolizing microorganism (e.g., methanotroph) can also over-express fabB (encoding β-ketoacyl-ACP synthase I, Accession No. EC:2.3.1.41), sfa (encoding a suppressor of fabA), and gnsA and gnsB (both encoding secG null mutant suppressors, i.e., cold shock proteins). In some examples, an endogenous fabF gene can be attenuated, which can increase the percentage of palmitoleate ($C_{16:1}$) produced.

In another example, a desired fatty acid derivative is a hydroxylated fatty acid. Hydroxyl modification can occur throughout the chain using specific enzymes. In particular, ω-hydroxylation produces a particularly useful molecule containing functional groups at both ends of the molecule (e.g., allowing for linear polymerization to produce polyester plastics). In certain embodiments, a $C_1$ metabolizing microorganism (e.g., methanotroph) may comprise one or more modified CYP52A type cytochrome P450 selected from CYP52A13, CYP52A14, CYP52A17, CYP52A18, CYP52A12, and CYP52A12B, wherein the cytochrome modifies fatty acids into, for example, ω-hydroxy fatty acids. Different fatty acids are hydroxylated at different rates by different cytochrome P450s. To achieve efficient hydroxylation of a desired fatty acid feedstock, $C_1$ metabolizing microorganisms are generated to express one or more P450 enzymes that can ω-hydroxylate a wide range of highly abundant fatty acid substrates. Of particular interest are P450 enzymes that catalyze ω-hydroxylation of lauric acid ($C_{12:0}$), myristic acid ($C_{14}$:0), palmitic acid ($C_{16:0}$), stearic acid ($C_{18:0}$), oleic acid ($C_{18:1}$), linoleic acid ($C_{18:2}$), and α-linolenic acid (ω3, $C_{18:3}$). Examples of P450 enzymes with known ω-hydroxylation activity on different fatty acids that may be cloned into a $C_1$ metabolizing non-photosynthetic microorganism include CYP94A1 from *Vicia sativa* (Tijet et al., *Biochem. J.* 332:583, 1988); CYP 94A5 from *Nicotiana tabacum* (Le Bouquin et al., *Eur. J. Biochem.* 268:3083, 2001); CYP78A1 from *Zea mays* (Larkin, *Plant Mol. Biol.* 25:343, 1994); CYP 86A1 (Benveniste et al., *Biochem. Biophys. Res. Commun.* 243:688, 1998) and CYP86A8 (Wellesen et al., *Proc. Nat'l. Acad. Sci. USA* 98:9694, 2001) from *Arabidopsis thaliana*; CYP 92B1 from *Petunia hybrida* (Petkova-Andonova et al., *Biosci. Biotechnol. Biochem.* 66:1819, 2002); CYP102A1 (BM-3) mutant F87 from *Bacillus megaterium* (Oliver et al., *Biochem.* 36:1567, 1997); and CYP 4 family from mammal and insect (Hardwick, *Biochem. Pharmacol.* 75:2263, 2008).

In certain embodiments, a $C_1$ metabolizing non-photosynthetic microorganisms comprises a nucleic acid molecule encoding a P450 enzyme capable of introducing additional internal hydroxylation at specific sites of fatty acids or ω-hydroxy fatty acids, wherein the recombinant $C_1$ metabolizing microorganisms can produce internally oxidized fatty acids or ω-hydroxy fatty acids or aldehydes or dicarboxylic acids. Examples of P450 enzymes with known in-chain hydroxylation activity on different fatty acids that may be used in $C_1$ metabolizing microorganisms of this disclosure include CYP81B1 from *Helianthus tuberosus* with ω-1 to ω-5 hydroxylation (Cabello-Hurtado et al., *J. Biol. Chem.* 273:7260, 1998); CYP790C1 from *Helianthus tuberosus* with ω-1 and ω-2 hydroxylation (Kandel et al., *J. Biol. Chem.* 280:35881, 2005); CYP726A1 from *Euphorbia lagscae* with epoxidation on fatty acid unsaturation (Cahoon et al., *Plant Physiol.* 128:615, 2002); CYP152B1 from *Sphingomonas paucimobilis* with α-hydroxylation (Matsunaga et al., *Biomed. Life Sci.* 35:365, 2000); CYP2E1 and 4A1 from human liver with ω-1 hydroxylation (Adas et al., *J. Lip. Res.* 40:1990, 1999); P450$_{BSβ}$ from *Bacillus subtilis* with α- and β-hydroxylation (Lee et al., *J. Biol. Chem.* 278:9761, 2003); and CYP102A1 (BM-3) from *Bacillus megaterium* with ω-1, ω-2 and ω-3 hydroxylation (Shirane et al., *Biochem.* 32:13732, 1993).

In certain embodiments, a $C_1$ metabolizing non-photosynthetic microorganisms comprises a nucleic acid molecule encoding a P450 enzyme capable of modifying fatty acids to comprise a ω-hydroxylation can be further modified to further oxidize the ω-hydroxy fatty acid derivative to yield dicarboxylic acids. In many cases, a P450 enzyme capable of performing the hydroxylation in the first instance is also capable of performing further oxidation to yield a dicarboxylic acid. In other embodiments, non-specific native alcohol dehydrogenases in the host organism may oxidize the ω-hydroxy fatty acid to a dicarboxylic acid. In further embodiments, a $C_1$ metabolizing non-photosynthetic organism further comprises a nucleic acid molecule that encodes one or more fatty alcohol oxidases, (such as FAO1, FAO1B, FAO2, FAO2B) or alcohol dehydrogenases (such as ADH-A4, ADH-A4B, ADH-B4, ADH-B4B, ADH-A10 and ADH-B11) (e.g., from *Candida tropicalis* as listed in U.S. Patent Application Publication 2010/0291653, which list is incorporated herein in its entirety) to facilitate production of dicarboxylic acids.

The methods described herein permit production of fatty esters and fatty acid derivatives having varied carbon chain lengths. Chain length is controlled by thioesterase, which is produced by expression of the tes and fat gene families. By expressing specific thioesterases, fatty acid derivatives having a desired carbon chain length can be produced. Non-limiting examples of suitable thioesterases are described herein and listed in U.S. Pat. No. 8,283,143 (FIG. 1, which figure is herein incorporated by reference). A nucleic acid molecule encoding a particular thioesterase may be introduced into a $C_1$ metabolizing microorganism (e.g., methanotroph) so that a fatty acid derivative of a particular carbon chain length is produced. In certain embodiments, expression of endogenous thioesterases are inhibited, suppressed, or down-regulated.

In certain embodiments, a fatty acid derivative has a carbon chain of about 8 to 24 carbon atoms, about 8 to 18 carbon atoms, about 10 to 18 carbon atoms, about 10 to 16 carbon atoms, about 12 to 16 carbon atoms, about 12 to 14 carbon atoms, about 14 to 24 carbon atoms, about 14 to 18 carbon atoms, about 8 to 16 carbon atoms, or about 8 to 14 carbon atoms. In alternative embodiments, a fatty acid derivative has a carbon chain of less than about 20 carbon atoms, less than about 18 carbon atoms, less than about 16 carbon atoms, less than about 14 carbon atoms, or less than about 12 carbon atoms. In other embodiments, a fatty ester product is a saturated or unsaturated fatty ester product having a carbon atom content between 8 and 24 carbon atoms. In further embodiments, a fatty ester product has a carbon atom content between 8 and 14 carbon atoms. In still further embodiments, a fatty ester product has a carbon content of 14 and 20 carbons. In yet other embodiments, a fatty ester is the methyl ester of $C_{18:1}$. In further embodiments, a fatty ester is the ethyl ester of $C_{16:1}$. In other embodiments, a fatty ester is the methyl ester of $C_{16:1}$. In yet other embodiments, a fatty ester is octadecyl ester of octanol.

Some microorganisms preferentially produce even- or odd-numbered carbon chain fatty acids and fatty acid derivatives. For example, *E. coli* normally produce even-numbered carbon chain fatty acids and fatty acid ethyl esters (FAEE). In certain embodiments, the methods disclosed herein may be used to alter that production in $C_1$ metabolizing microorganisms (e.g., methanotrophs) such that $C_1$ metabolizing microorganisms (e.g., methanotrophs) can be made to produce odd-numbered carbon chain fatty acid derivatives.

An ester includes what may be designated an "A" side and a "B" side. The B side may be contributed by a fatty acid produced from de novo synthesis in a $C_1$ metabolizing microorganism (e.g., methanotroph) of this disclosure. In some embodiments where a $C_1$ metabolizing microorganism (e.g., methanotroph) is additionally engineered to make alcohols, including fatty alcohols, the A side is also produced by a $C_1$ metabolizing microorganism (e.g., methanotroph). In yet other embodiments, the A side can be provided in the medium. By selecting a desired thioesterase encoding nucleic acid molecule, a B side (and an A side when fatty alcohols are being made) can be designed to be have certain carbon chain characteristics. These characteristics include points of branching, unsaturation, and desired carbon chain lengths.

When particular thioesterase genes are selected, the A and B side will have similar carbon chain characteristics when they are both contributed by a $C_1$ metabolizing microorganism (e.g., methanotroph) using fatty acid biosynthetic pathway intermediates. For example, at least about 50%, 60%, 70%, or 80% of the fatty esters produced will have A sides and B sides that vary by about 2, 4, 6, 8, 10, 12, or 14 carbons in length. The A side and the B side can also display similar branching and saturation levels.

In addition to producing fatty alcohols for contribution to the A side, a $C_1$ metabolizing microorganism (e.g., methanotroph) can produce other short chain alcohols, such as ethanol, propanol, isopropanol, isobutanol, and butanol for incorporation on the A side. For example, butanol can be made by a $C_1$ metabolizing microorganism (e.g., methanotroph). To create butanol producing cells, a $C_1$ metabolizing microorganism (e.g., methanotroph), for example, can be further engineered to express atoB (acetyl-CoA acetyltransferase) from *Escherichia coli* K12, β-hydroxybutyryl-CoA dehydrogenase from *Butyrivibrio fibrisolvens*, crotonase from *Clostridium beijerinckii*, butyryl CoA dehydrogenase from *Clostridium beijerinckii*, CoA-acylating aldehyde dehydrogenase (ALDH) from *Cladosporium fulvum*, and adhE encoding an aldehyde-alcohol dehydrogenase of *Clostridium acetobutylicum* in, for example, a pBAD24 expression vector under a prpBCDE promoter system. $C_1$ metabolizing microorganisms (e.g., methanotrophs) may be similarly modified to produce other short chain alcohols. For example, ethanol can be produced in a production host using the methods taught by Kalscheuer et al. (*Microbiol.* 152: 2529, 2006).

$C_1$ Metabolizing Microorganisms—Host Cells

The $C_1$ metabolizing microorganisms of the instant disclosure may be a natural strain, strain adapted (e.g., performing fermentation to select for strains with improved growth rates and increased total biomass yield compared to the parent strain), or recombinantly modified to produce fatty acid derivatives of interest or to have increased growth rates or both (e.g., genetically altered to express a fatty acyl-CoA reductase, a thioesterase, acyl-CoA synthetase, or a combination thereof). In certain embodiments, the $C_1$ metabolizing microorganisms are not photosynthetic microorganisms, such as algae or plants.

In certain embodiments, the present disclosure provides $C_1$ metabolizing microorganisms that are prokaryotes or bacteria, such as *Methylomonas*, *Methylobacter*, *Methylococcus*, *Methylosinus*, *Methylocystis*, *Methylomicrobium*, *Methanomonas*, *Methylophilus*, *Methylobacillus*, *Methylobacterium*, *Hyphomicrobium*, *Xanthobacter*, *Bacillus*, *Paracoccus*, *Nocardia*, *Arthrobacter*, *Rhodopseudomonas*, or *Pseudomonas*.

In further embodiments, the $C_1$ metabolizing bacteria are a methanotroph or a methylotroph. Exemplary methanotrophs include *Methylomonas*, *Methylobacter*, *Methylococcus*, *Methylosinus*, *Methylocystis*, *Methylomicrobium*, *Methanomonas*, *Methylocella*, or a combination thereof. Exemplary methylotrophs include *Methylobacterium extorquens*, *Methylobacterium radiotolerans*, *Methylobacterium Methylobacterium chloromethanicum*, *Methylobacterium nodulans*, or a combination thereof.

In certain embodiments, methanotrophic bacteria are genetically engineered with the capability to convert $C_1$ substrate feedstock into fatty alcohols. Methanotrophic bacteria have the ability to oxidize methane as a carbon and energy source. Methanotrophic bacteria are classified into three groups based on their carbon assimilation pathways and internal membrane structure: type I (gamma proteobacteria), type II (alpha proteobacteria, and type X (gamma proteobacteria). Type I methanotrophs use the ribulose monophosphate (RuMP) pathway for carbon assimilation whereas type II methanotrophs use the serine pathway. Type X methanotrophs use the RuMP pathway but also express low levels of enzymes of the serine pathway. Methanotrophic bacteria include obligate methanotrophs, which can only utilize C1 substrates for carbon and energy sources, and facultative methanotrophs, which naturally have the ability to utilize some multi-carbon substrates as a sole carbon and energy source.

Exemplary facultative methanotrophs include some species of *Methylocella*, *Methylocystis*, and *Methylocapsa* (e.g., *Methylocella silvestris*, *Methylocella palustris*, *Methylocella tundrae*, *Methylocystis daltona* strain SB2, *Methylocystis bryophila*, and *Methylocapsa aurea* KYG), *Methylobacterium organophilum* (ATCC 27,886), *Methylibium petroleiphilum*, or high growth variants thereof. Exemplary obligate methanotrophic bacteria include: *Methylococcus capsulatus* Bath, *Methylomonas* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylomonas flagellata* sp AJ-3670 (FERM P-2400), *Methylacidiphilum infernorum* and *Methylomicrobium alcaliphilum*, or a high growth variants thereof.

In still further embodiments, the present disclosure provides $C_1$ metabolizing microorganisms that are syngas metabolizing bacteria, such as *Clostridium*, *Moorella*, *Pyrococcus*, *Eubacterium*, *Desulfobacterium*, *Carboxydothermus*, *Acetogenium*, *Acetobacterium*, *Acetoanaerobium*, *Butyribaceterium*, *Peptostreptococcus*, or a combination thereof. Exemplary methylotrophs include *Clostridium autoethanogenum*, *Clostridium ljungdahli*, *Clostridium ragsdalei*, *Clostridium carboxydivorans*, *Butyribacterium methylotrophicum*, *Clostridium woodii*, *Clostridium neopropanologen*, or a combination thereof.

In certain other embodiments, $C_1$ metabolizing non-photosynthetic microorganisms are eukaryotes such as yeast, including *Candida*, *Yarrowia*, *Hansenula*, *Pichia*, *Torulopsis*, or *Rhodotorula*.

In certain other embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acyl-CoA reductase, a thioesterase, acyl-CoA synthetase, a combination thereof, or all three.

$C_1$ Metabolizing Microorganisms—Non-Natural or Recombinant

In some embodiments, as described herein, there are provided recombinant $C_1$ metabolizing microorganisms (e.g., non-natural methanotroph bacteria) may have a fatty acyl-CoA reductase (FAR) that utilize a $C_1$ substrate feedstock (e.g., methane) to generate $C_8$ to $C_{24}$ fatty acid derivatives, such as fatty alcohol. In various embodiments, a recombinant $C_1$ metabolizing microorganism expresses or over expresses a nucleic acid molecule that encodes a FAR enzyme. In certain embodiments, a FAR enzyme may be endogenous to the $C_1$ metabolizing microorganism or a FAR enzyme may be heterologous to the $C_1$ metabolizing microorganism.

In one aspect, the present disclosure provides a non-natural methanotroph having a recombinant nucleic acid molecule encoding a fatty acid converting enzyme, wherein the methanotroph is capable of converting a $C_1$ substrate into a $C_8$-$C_{24}$ fatty aldehyde, fatty alcohol, fatty ester wax, hydroxy fatty acid, dicarboxylic acid, or a combination thereof. In certain embodiments, the non-natural methanotroph contains a fatty acid converting enzyme that is an acyl-CoA dependent fatty acyl-CoA reductase, such as acr1, FAR, CER4 (Genbank Accession No. JN315781.1), or Maqu_2220, capable of forming a fatty alcohol. In certain embodiments, the non-natural methanotroph contains a fatty acid converting enzyme that is an acyl-CoA dependent fatty acyl-CoA reductase capable of forming a fatty aldehyde, such as acr1. In some embodiments, the process will result in the production of fatty alcohols comprising $C_8$, $C_{10}$, $C_{12}$, $C_{14}$, $C_{16}$, $C_{18}$, $C_{20}$, $C_{22}$ or $C_{24}$ carbons in length.

In any of the aforementioned recombinant $C_1$ metabolizing microorganisms capable of producing fatty acid derivatives (e.g., fatty alcohols) as encompassed by the present disclosure, the non-natural methanotrophs further comprise a recombinant nucleic acid molecule encoding a thioesterase, such as a tesA lacking a leader sequence, UcFatB, or BTE. In certain embodiments, the endogenous thioesterase activity is reduced, minimal or abolished as compared to unaltered endogenous thioesterase activity.

In any of the aforementioned recombinant $C_1$ metabolizing microorganisms capable of producing fatty acid derivatives (e.g., fatty alcohols) as encompassed by the present disclosure, the non-natural methanotrophs further comprise a recombinant nucleic acid molecule encoding an acyl-CoA synthetase, such as FadD, yng1, or FAA2. In certain embodiments, the endogenous acyl-CoA synthetase activity is reduced, minimal or abolished as compared to unaltered endogenous acyl-CoA synthetase activity.

In further embodiments, the present disclosure provides a non-natural methanotroph having a recombinant nucleic acid molecule encoding a heterologous acyl-CoA dependent fatty acyl-CoA reductase, a recombinant nucleic acid molecule encoding a heterologous thioesterase, and a recombinant nucleic acid molecule encoding a heterologous acyl-CoA synthetase, wherein the methanotroph is capable of converting a $C_1$ substrate into a $C_8$-$C_{24}$ fatty alcohol. In certain embodiments, the fatty acyl-CoA reductase is over-expressed in the non-natural methanotroph as compared to the expression level of the native fatty acyl-CoA reductase. In certain embodiments, the acyl-CoA dependent fatty acyl-CoA reductase capable of forming a fatty aldehyde, fatty alcohol, or both is acr1, or the acyl-CoA independent fatty acyl-CoA reductase capable of forming a fatty alcohol is FAR, CER4, or Maqu_2220. In certain embodiments, the acyl-CoA synthetase is FadD, yng1, or FAA2.

In still further embodiments, there is provided a non-natural methanotroph having a recombinant nucleic acid molecule encoding a heterologous acyl-CoA independent fatty acyl-CoA reductase, and a recombinant nucleic acid molecule encoding a heterologous thioesterase, wherein the methanotroph is capable of converting a $C_1$ substrate into a $C_8$-$C_{24}$ fatty alcohol. In certain embodiments, the fatty acyl-CoA reductase is over-expressed in the non-natural methanotroph as compared to the expression level of the native fatty acyl-CoA reductase.

Any of the aforementioned recombinant $C_1$ metabolizing microorganisms (e.g., non-natural methanotroph bacteria) may have a FAR enzyme or functional fragment thereof can be derived or obtained from a species of *Marinobacter*, such as *M. algicola*, *M. alkaliphilus*, *M. aquaeolei*, *M. arcticus*, *M. bryozoorum*, *M. daepoensis*, *M. excellens*, *M. flavimaris*, *M. guadonensis*, *M. hydrocarbonoclasticus*, *M. koreenis*, *M. lipolyticus*, *M. litoralis*, *M. lutaoensis*, *M. maritimus*, *M. sediminum*, *M. squalenivirans*, *M. vinifirmus*, or equivalent and synonymous species thereof. In certain embodiments, a FAR enzyme for use in the compositions and methods disclosed herein is from marine bacterium *Marinobacter algicola* DG893 (Genbank Accession No. EDM49836.1, FAR "Maa_893") or *Marinobacter aquaeolei* VT8 (Genbank Accession No. YP_959486.1, FAR "Maqu_2220") or *Oceanobacter* sp. RED65 (Genbank Accession No. EAT13695.1, FAR "Ocs_65").

In still further embodiments of any of the aforementioned recombinant $C_1$ metabolizing microorganisms (e.g., non-natural methanotroph bacteria), a FAR enzyme or functional fragment thereof is FAR_Hch (*Hahella chejuensis* KCTC 2396, GenBank Accession No. YP_436183.1); FAR_Act (from marine Actinobacterium strain PHSC20C1, GenBank Accession No. EAR25464.1), FAR_Mme (marine metagenome, GenBank Accession No. EDD40059.1), FAR_Aec (*Acromyrmex echinatior*, GenBank Accession No. EGI61731.1), FAR_Cfl (*Camponotus floridanus*, GenBank Accession No. EFN62239.1), and FAR_Sca (*Streptomyces cattleya* NRRL 8057, GenBank Accession No. YP_006052652.1). In other embodiments, a FAR enzyme or functional fragment thereof is isolated or derived from *Vitis vinifera* (FAR_Vvi, GenBank Accession No. CAO22305.1 or CAO67776.1), *Desulfatibacillum alkenivorans* AK-01 (FAR_Dal, GenBank Accession No. YP_002430327.1), *Simmondsia chinensis* (FAR_Sch, GenBank Accession No. AAD38039.1), *Bombyx mori* (FAR_Bmo, GenBank Accession No. BAC79425.1), *Arabidopsis thaliana* (FAR_Ath; GenBank Accession No. DQ446732.1 or NM_115529.1), or *Ostrinia scapulalis* (FAR_Osc; GenBank Accession no. EU817405.1).

In certain embodiments, a FAR enzyme or functional fragment thereof is derived or obtained from *M. algicola* DG893 or *Marinobacter aquaeolei* YT8 and has an amino acid sequence that is at least at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. EDM49836.1 or YP_959486.1, respectively, or a functional fragment thereof. In another embodiment, the recombinant encoded FAR enzyme has an amino acid sequence that is identical to the sequence set forth in Genbank Accession No. EDM49836.1 or YP_959486.1.

In certain embodiments, recombinant $C_1$ metabolizing microorganisms capable of producing fatty acid derivatives (e.g., fatty alcohols) as encompassed by the present disclosure will include heterologous nucleic acid molecules encoding a carboxylic acid reductase (CAR). In some embodiments, recombinant microorganisms will additionally comprise one or more heterologous nucleic acid molecules selected from an acyl-ACP thioesterase (TE), alcohol dehydrogenase (ADH), or phosphopantetheinyl transferase (PPTase), as further described herein.

The present disclosure provides a process for using a recombinant $C_1$ metabolizing microorganism or non-natural methanotroph to convert a $C_1$ substrate (e.g., natural gas, methane) into $C_8$-$C_{24}$ fatty alcohols. Microorganisms have evolved efficient processes for the conversion of carbon sources to fatty aldehydes, fatty alcohols, fatty ester wax, hydroxy fatty acids, dicarboxylic acids, branched fatty acids, or the like. The presently disclosed process exploits such efficiency by diverting the fatty acids so produced to generate derivatives, such as long chain fatty alcohols, by metabolic engineering of a host $C_1$ metabolizing microorganism. In one aspect, this is accomplished by developing a pathway within a recombinant $C_1$ metabolizing host cell or a non-natural methanotroph. For example, the enzymes of the pathway may include an acyl-ACP thioesterase (TE), a carboxylic acid reductase (CAR), and a ketoreductase/alcohol dehydrogenase (ADH). In a preferred embodiment, a CAR will be heterologous to the host cell. In some embodiments, a recombinant $C_1$ metabolizing microorganism or non-natural methanotroph will include at least one additional heterologous nucleic acid molecule encoding a polypeptide selected from the set of enzymes comprising acyl-ACP thioesterase (TE), alcohol dehydrogenase/ketoreductase (ADH), or both. In some embodiments, the pathway is engineered in a $C_1$ metabolizing bacterial host cell, such as a methanotroph host cell.

Carboxylic acid reductases (CARs) are unique ATP- and NADPH-dependent enzymes that reduce carboxylic acids, such as fatty acids to the corresponding aldehyde. CARs are multi-component enzymes comprising a reductase domain; an adenylation domain and a phosphopantetheine attachment site. As disclosed herein, fatty acids, such as those fatty acids comprising 8 to 24 carbon atoms and particularly those fatty acids comprising 12 carbon atoms (dodecanoic acid) to 18 carbon atoms (stearic acid) may be reduced by a carboxylic acid reductase or variant thereof of this disclosure, such as those having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the CAR of *Mycobacterium* sp. JLS, *Nocardia* sp. NRRL5646, or *Streptomyces griseus*.

In some embodiments, a variant CAR comprises at least 90% (e.g., at least 91%, at least 92%, at least 93%, at least 94%, at least 95%, at least 96%, at least 97%, at least 98%, or at least 99%) sequence identity with CAR from *Mycobacterium* sp. JLS and a substitution of an amino acid at a position corresponding to position 8270, A271, K274, A275, P467, Q584, E626, and/or D701 when aligned with CAR from *Mycobacterium* sp. JLS. In certain embodiments, a variant CAR may include an amino acid sequence that is at least 85%, (e.g., at least 86%, at least 87%, at least 88%, at least 89%, at least 90%, at least 91%, at least 92%, at least 93%, at least 94%, at least 95%, at least 96%, at least 97%, at least 98% and at least 99%) identical to CAR from *Mycobacterium* sp. JLS and an amino acid substitution corresponding to R270W, A271W, K274(G/N/V/I/W/L/M/Q/S), A275F, P467S, Q584R, E626G, D701G, K274L/A369T/L380Y, K274LN358H/E845A, K274M/T282K, K274Q/T282Y, K274S/A715T, K274W/L380G/A477T, K274W/T282E/L380V, K274W/T282Q, K274W/V358R and/or R43c/K274I in CAR from *Mycobacterium* sp. JLS. In certain embodiments, a variant CAR will comprise an amino acid substitution at position K274 and one or more (e.g., 1, 2 or 3) further amino acid substitutions when the variant is aligned with CAR from *Mycobacterium* sp. JLS. In some embodiments, CAR activity of the variant will be greater than CAR activity of a reference or parent sequence. CAR activity can be determined, for example, by assays known in the art (see, e.g., U.S. Patent Application Publication No. 2010/0298612).

In some embodiments, a variant CAR may encompass additional amino acid substitutions at positions other than those listed herein, including, for example, variants having one or more conservative substitutions. In certain embodiments, conservatively substituted variants of a CAR will include substitutions of a small percentage, such as less than 5%, less than 4%, less than 3%, less than 2%, or less than 1% of the amino acids of a CAR polypeptide sequence.

As noted herein, intracellular expression of a carboxylic acid reductase of this disclosure will lead to production not only of the fatty aldehyde but also the corresponding fatty alcohol. This is the result of alcohol dehydrogenase activity within a recombinant host cell. In some embodiments, the process will result in the production of fatty alcohols comprising $C_8$, $C_{10}$, $C_{12}$, $C_{14}$, $C_{16}$, $C_{18}$, $C_{20}$, $C_{22}$ or $C_{24}$ carbons in length.

In still further embodiments, there is provided a $C_1$ metabolizing microorganism or non-natural methanotroph having a recombinant nucleic acid molecule encoding a carboxylic acid reductase, a recombinant nucleic acid molecule encoding a phosphopantetheinyl tranferase, and a recombinant nucleic acid molecule encoding an alcohol dehydrogenase, wherein the methanotroph is capable of converting a $C_1$ substrate into a $C_8$-$C_{24}$ fatty alcohol.

In another aspect, this disclosure provides any of the aforementioned $C_1$ metabolizing microorganism or non-natural methanotrophs further comprise a recombinant nucleic acid molecule encoding a P450 enzyme or monoxygenase enzyme to produce an ω-hydroxy fatty acid. In certain embodiments, the endogenous alcohol dehydrogenase activity is inhibited as compared to unaltered endogenous alcohol dehydrogenase activity. In other embodiments, the endogenous alcohol dehydrogenase activity is increased or elevated as compared to unaltered endogenous alcohol dehydrogenase activity to produce dicarboxylic acid.

In any of the aforementioned non-natural methanotrophs, a fatty alcohol is produced comprising one or more of $C_8$-$C_{14}$ or $C_{10}$-$C_{16}$ or $C_{12}$-$C_{14}$ or $C_{14}$-$C_{18}$ or $C_{14}$-$C_{24}$ fatty alcohols. In certain embodiments, the methanotroph produces fatty alcohol comprising $C_{10}$ to $C_{18}$ fatty alcohol and the $C_{10}$ to $C_{18}$ fatty alcohols comprise at least 70% of the total fatty alcohol. In further embodiments, the methanotroph produces fatty alcohol comprising a branched chain fatty alcohol.

In any of the aforementioned non-natural methanotrophs, the amount of fatty aldehyde, fatty alcohol, fatty acid, or dicarboxylic acid produced by the non-natural methanotroph ranges from about 1 mg/L to about 500 g/L. In certain other embodiments, a $C_1$ substrate feedstock for a $C_1$ metabolizing microorganism or non-natural methanotroph as described is methane, methanol, formaldehyde, formic acid or a salt thereof, carbon monoxide, carbon dioxide, a methylamine, a methylthiol, a methylhalogen, natural gas, or unconventional natural gas. In certain embodiments, a $C_1$ metabolizing microorganism or non-natural methanotroph is capable of converting natural gas, unconventional natural gas or syngas (or syngas comprising methane) into a $C_8$-$C_{18}$ fatty aldehyde, fatty alcohol, hydroxy fatty acid, or dicarboxylic acid.

In still further embodiments, there is provided a $C_1$ metabolizing microorganism or non-natural methanotroph having a recombinant nucleic acid molecule encoding a heterologous fatty acyl-CoA reductase, a recombinant nucleic acid molecule encoding a heterologous thioesterase, and a recombinant nucleic acid molecule encoding a heterologous P450 or monooxygenase, wherein the native alcohol dehydrogenase is inhibited, and wherein the $C_1$ metabolizing microorganism or methanotroph is capable of converting a $C_1$ substrate into a $C_8$-$C_{24}$ ω-hydroxy fatty acid.

In still further embodiments, there is provided a $C_1$ metabolizing microorganism or non-natural methanotroph having a recombinant nucleic acid molecule encoding a heterologous fatty acyl-CoA reductase, and a recombinant nucleic acid molecule encoding a heterologous thioesterase, wherein the methanotroph is over-expressing native alcohol dehydrogenase as compared to the normal expression level of native alcohol dehydrogenase, transformed with a recombinant nucleic acid molecule encoding a heterologous alcohol dehydrogenase, or both, and wherein the $C_1$ metabolizing microorganism or methanotroph is capable of converting a $C_1$ substrate into a $C_8$-$C_{24}$ dicarboxylic acid alcohol.

In any of the aforementioned $C_1$ metabolizing microorganisms or non-natural methanotrophs, the host methanotroph can be *Methylococcus capsulatus* Bath strain, *Methylomonas* 16a (ATCC PTA 2402), *Methylosinus trichosporium* OB3b (NRRL B-11,196), *Methylosinus sporium* (NRRL B-11,197), *Methylocystis parvus* (NRRL B-11, 198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris*, *Methylocella palustris* (ATCC 700799), *Methylocella tundrae*, *Methylocystis daltona* strain SB2, *Methylocystis bryophila*, *Methylocapsa aurea* KYG, *Methylacidiphilum infernorum*, *Methylibium petroleiphilum*, *Methylomicrobium alcaliphilum*, or a combination thereof.

Any of the aforementioned $C_1$ metabolizing microorganisms or non-natural methanotroph bacteria may also have undergone strain adaptation under selective conditions to produce variants with improved properties for fatty acid derivative production, before or after introduction of the recombinant nucleic acid molecules. Improved properties may include increased growth rate, yield of desired products (e.g., fatty alcohols), or tolerance to process or culture contaminants. In particular embodiments, a high growth variant $C_1$ metabolizing microorganism or methanotroph comprises a host bacteria that is capable of growing on a methane feedstock as a primary carbon and energy source and that possesses a faster exponential phase growth rate (i.e., shorter doubling time) than its parent, reference, or wild-type bacteria (see, e.g., U.S. Pat. No. 6,689,601).

Each of the microorganisms of this disclosure may be grown as an isolated culture, with a heterologous organism that may aid with growth, or one or more of these bacteria may be combined to generate a mixed culture. In still further embodiments, $C_1$ metabolizing non-photosynthetic microorganisms of this disclosure are obligate $C_1$ metabolizing non-photosynthetic microorganisms.

$C_1$ Metabolizing Microorganisms—Producing Fatty Acid Derivatives

In another aspect, as described herein, there are provided methods for making fatty acid derivatives by culturing a non-natural $C_1$ metabolizing non-photosynthetic microorganism with a $C_1$ substrate feedstock and recovering the fatty acid derivative, wherein the $C_1$ metabolizing non-photosynthetic microorganism comprises a recombinant nucleic acid molecule encoding a fatty acid converting enzyme, and wherein the $C_1$ metabolizing non-photosynthetic microorganism converts the $C_1$ substrate into a $C_8$-$C_{24}$ fatty acid derivative comprising a fatty aldehyde, a fatty alcohol, a hydroxy fatty acid, a dicarboxylic acid, or a combination thereof.

In certain embodiments, the $C_1$ metabolizing non-photosynthetic microorganism being cultured is *Methylomonas*, *Methylobacter*, *Methylococcus*, *Methylosinus*, *Methylocystis*, *Methylomicrobium*, *Methanomonas*, *Methylophilus*, *Methylobacillus*, *Methylobacterium*, *Hyphomicrobium*, *Xanthobacter*, *Bacillus*, *Paracoccus*, *Nocardia*, *Arthrobacter*, *Rhodopseudomonas*, *Pseudomonas*, *Candida*, *Yarrowia*, *Hansenula*, *Pichia*, *Torulopsis*, or *Rhodotorula*. In further embodiments, $C_1$ metabolizing non-photosynthetic microorganism being cultured is bacteria, such as a methanotroph or methylotroph.

The methanotroph may be a *Methylomonas* sp. 16a (ATCC PTA 2402), *Methylosinus trichosporium* (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11, 200), *Methylobacter capsulatus* (NRRL B-11,201), *Methylobacterium organophilum* (ATCC 27,886), *Methylomonas* sp. AJ-3670 (FERM P-2400), *Methylocella silvestris*, *Methylacidiphilum infernorum*, *Methylibium petroleiphilum*, or a combination thereof. In certain embodiments, the methanotroph culture further comprises one or more heterologous bacteria.

The methylotroph may be a *Methylobacterium extorquens*, *Methylobacterium radiotolerans*, *Methylobacterium populi*, *Methylobacterium chloromethanicum*, *Methylobacterium nodulans*, or a combination thereof.

In further embodiments, the $C_1$ metabolizing microorganism or bacteria can metabolize natural gas, unconventional natural gas, or syngas. In certain embodiments, the syngas metabolizing bacteria include *Clostridium autoethanogenum*, *Clostridium ljungdahli*, *Clostridium ragsdalei*, *Clostridium carboxydivorans*, *Butyribacterium methylotrophicum*, *Clostridium woodii*, *Clostridium neopropanologen*, or a combination thereof. In certain other embodiments, the metabolizing non-photosynthetic microorganism is an obligate $C_1$ metabolizing non-photosynthetic microorganism. In certain other embodiments, the metabolizing non-photosynthetic microorganism is an facultative $C_1$ metabolizing non-photosynthetic microorganism.

In any of the aforementioned methods, the cultured $C_1$ metabolizing microorganism contains a fatty acid converting enzyme that is an acyl-CoA dependent fatty acyl-CoA reductase, such as acr1, FAR, CER4 (Genbank Accession No. JN315781.1), or Maqu_2220, capable of forming a fatty alcohol. In certain embodiments, the $C_1$ metabolizing microorganism being cultured contains a fatty acid converting enzyme that is an acyl-CoA dependent fatty acyl-CoA reductase capable of forming a fatty aldehyde, such as acr1. In some embodiments, the process will result in the production of fatty alcohols comprising $C_8$, $C_{10}$, $C_{12}$, $C_{14}$, $C_{16}$, $C_{18}$, $C_{20}$, $C_{22}$ or $C_{24}$ carbons in length.

In any of the aforementioned recombinant $C_1$ metabolizing microorganisms capable of producing fatty acid derivatives (e.g., fatty alcohols) as encompassed by the present methods, the $C_1$ metabolizing microorganisms further comprise a recombinant nucleic acid molecule encoding a thioesterase, such as a tesA lacking a leader sequence, UcFatB, or BTE. In certain embodiments, the endogenous thioesterase activity is reduced, minimal or abolished as compared to unaltered endogenous thioesterase activity.

In any of the aforementioned recombinant $C_1$ metabolizing microorganisms capable of producing fatty acid derivatives (e.g., fatty alcohols) as encompassed by the present methods, the $C_1$ metabolizing microorganisms further comprise a recombinant nucleic acid molecule encoding an acyl-CoA synthetase, such as FadD, yng1, or FAA2. In certain embodiments, the endogenous acyl-CoA synthetase activity is reduced, minimal or abolished as compared to unaltered endogenous acyl-CoA synthetase activity.

In further embodiments, the present methods provide a $C_1$ metabolizing microorganism having a recombinant nucleic acid molecule encoding a heterologous acyl-CoA dependent fatty acyl-CoA reductase, a recombinant nucleic acid molecule encoding a heterologous thioesterase, and a recombinant nucleic acid molecule encoding a heterologous acyl-CoA synthetase, wherein the $C_1$ metabolizing microorganism is capable of converting a $C_1$ substrate into a $C_8$-$C_{24}$ fatty alcohol. In certain embodiments, the fatty acyl-CoA reductase is over-expressed in the cultured $C_1$ metabolizing microorganism as compared to the expression level of the native fatty acyl-CoA reductase. In certain embodiments, the acyl-CoA dependent fatty acyl-CoA reductase capable of forming a fatty aldehyde, fatty alcohol, or both is acr1, or the acyl-CoA independent fatty acyl-CoA reductase capable of forming a fatty alcohol is FAR, CER4, or Maqu_2220. In certain embodiments, the acyl-CoA synthetase is FadD, yng1, or FAA2.

In still further embodiments, the methods provide a $C_1$ metabolizing microorganism having a recombinant nucleic acid molecule encoding a heterologous acyl-CoA independent fatty acyl-CoA reductase, and a recombinant nucleic acid molecule encoding a heterologous thioesterase, wherein the methanotroph converts a $C_1$ substrate into a $C_8$-$C_{24}$ fatty alcohol. In certain embodiments, the fatty acyl-CoA reductase is over-expressed in the $C_1$ metabolizing microorganism as compared to the expression level of the native fatty acyl-CoA reductase.

In still further embodiments, the methods provide a cultured $C_1$ metabolizing microorganism having a recombinant nucleic acid molecule encoding a carboxylic acid reductase, a recombinant nucleic acid molecule encoding a phosphopantetheinyl tranferase, and a recombinant nucleic acid molecule encoding an alcohol dehydrogenase, wherein the methanotroph is capable of converting a $C_1$ substrate into a $C_8$-$C_{24}$ fatty alcohol.

In another aspect, the methods of this disclosure provide any of the aforementioned cultured $C_1$ metabolizing microorganisms further comprising a recombinant nucleic acid molecule encoding a P450 enzyme or monoxygenase enzyme to produce ω-hydroxy fatty acid. In certain embodiments, the endogenous alcohol dehydrogenase activity is inhibited as compared to unaltered endogenous alcohol dehydrogenase activity. In other embodiments, the endogenous alcohol dehydrogenase activity is increased or elevated as compared to unaltered endogenous alcohol dehydrogenase activity to produce dicarboxylic acid.

In any of the aforementioned cultured $C_1$ metabolizing microorganisms, the methods produce a fatty alcohol comprising one or more of $C_8$-$C_{14}$ or $C_{10}$-$C_{16}$ or $C_{12}$-$C_{14}$ or $C_{14}$-$C_{18}$ or $C_{14}$-$C_{24}$ fatty alcohols. In certain embodiments, the $C_1$ metabolizing microorganisms produce fatty alcohol comprising $C_{10}$ to $C_{18}$ fatty alcohol and the $C_{10}$ to $C_{18}$ fatty alcohols comprise at least 70% of the total fatty alcohol. In further embodiments, the $C_1$ metabolizing microorganisms produce fatty alcohol comprising a branched chain fatty alcohol.

In any of the aforementioned cultured $C_1$ metabolizing microorganism, the amount of fatty aldehyde, fatty alcohol, fatty acid, or dicarboxylic acid produced by the $C_1$ metabolizing microorganisms range from about 1 mg/L to about 500 g/L. In certain other embodiments, the $C_1$ substrate feedstock for the $C_1$ metabolizing microorganisms used in the methods of making fatty acid derivatives is methane, methanol, formaldehyde, formic acid or a salt thereof, carbon monoxide, carbon dioxide, a methylamine, a methylthiol, a methylhalogen, natural gas, or unconventional natural gas. In certain embodiments, the $C_1$ metabolizing microorganisms convert natural gas, unconventional natural gas or syngas comprising methane into a $C_8$-$C_{18}$ fatty aldehyde, fatty alcohol, hydroxy fatty acid, or dicarboxylic acid.

In still further embodiments, the methods provide a $C_1$ metabolizing microorganism having a recombinant nucleic acid molecule encoding a heterologous fatty acyl-CoA reductase, a recombinant nucleic acid molecule encoding a heterologous thioesterase, and a recombinant nucleic acid molecule encoding a heterologous P450 or monooxygenase, wherein the native alcohol dehydrogenase is inhibited, and wherein the $C_1$ metabolizing microorganism converts a $C_1$ substrate into a $C_8$-$C_{24}$ ω-hydroxy fatty acid.

In still further embodiments, the methods provide a $C_1$ metabolizing microorganism having a recombinant nucleic acid molecule encoding a heterologous fatty acyl-CoA reductase, and a recombinant nucleic acid molecule encoding a heterologous thioesterase, wherein the $C_1$ metabolizing microorganism over-expresses native alcohol dehydrogenase as compared to the normal expression level of native alcohol dehydrogenase, is transformed with a recombinant nucleic acid molecule encoding a heterologous alcohol dehydrogenase, or both, wherein the $C_1$ metabolizing microorganism is capable of converting a $C_1$ substrate into a $C_8$-$C_{24}$ dicarboxylic acid alcohol.

In any of the aforementioned methods, the $C_1$ metabolizing microorganisms can be cultured in a controlled culturing unit, such as a fermentor or bioreactor.

Codon Optimization

Expression of recombinant proteins is often difficult outside their original host. For example, variation in codon usage bias has been observed across different species of bacteria (Sharp et al., *Nucl. Acids. Res.* 33:1141, 2005). Over-expression of recombinant proteins even within their native host may also be difficult. In certain embodiments of the invention, nucleic acids (e.g., nucleic acids encoding fatty alcohol forming enzymes) that are to be introduced into host methanotrophic bacteria as described herein may undergo codon optimization to enhance protein expression. Codon optimization refers to alteration of codons in genes or coding regions of nucleic acids for transformation of a methanotrophic bacterium to reflect the typical codon usage of the host bacteria species without altering the polypeptide for which the DNA encodes. Codon optimization methods for optimum gene expression in heterologous hosts have been previously described (see, e.g., Welch et al., *PLoS One*

4:e7002, 2009; Gustafsson et al., *Trends Biotechnol*. 22:346, 2004; Wu et al., *Nucl. Acids Res*. 35:D76, 2007; Villalobos et al., *BMC Bioinformatics* 7:285, 2006; U.S. Patent Application Publication Nos. US 2011/0111413; US 2008/0292918; disclosure of which are incorporated herein by reference, in their entirety).

Transformation Methods

Any of the recombinant $C_1$ metabolizing microorganisms or methanotrophic bacteria described herein may be transformed to comprise at least one exogenous nucleic acid to provide the host bacterium with a new or enhanced activity (e.g., enzymatic activity) or may be genetically modified to remove or substantially reduce an endogenous gene function using a variety of methods known in the art.

Transformation refers to the transfer of a nucleic acid (e.g., exogenous nucleic acid) into the genome of a host cell, resulting in genetically stable inheritance. Host cells containing the transformed nucleic acid molecules are referred to as "non-naturally occurring" or "recombinant" or "transformed" or "transgenic" cells.

Expression systems and expression vectors useful for the expression of heterologous nucleic acids in $C_1$ metabolizing microorganisms or methanotrophic bacteria are known.

Electroporation of $C_1$ metabolizing bacteria has been previously described in Toyama et al., *FEMS Microbiol. Lett*. 166:1, 1998; Kim and Wood, *Appl. Microbiol. Biotechnol*. 48:105, 1997; Yoshida et al., *Biotechnol. Lett*. 23:787, 2001, and U.S. Patent Application Publication No. US 2008/0026005.

Bacterial conjugation, which refers to a particular type of transformation involving direct contact of donor and recipient cells, is more frequently used for the transfer of nucleic acids into $C_1$ metabolizing bacteria. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acid molecules into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilized plasmid. The physical transfer of the donor plasmid can occur through a self-transmissible plasmid or with the assistance of a "helper" plasmid. Conjugations involving $C_1$ metabolizing bacteria have been previously described in Stolyar et al., *Mikrobiologiya* 64:686, 1995; Motoyama et al., *Appl. Micro. Biotech*. 42:67, 1994; Lloyd et al., *Arch. Microbiol*. 171:364, 1999; and Odom et al., PCT Publication No. WO 02/18617; Ali et al., *Microbiol*. 152:2931, 2006.

Expression of heterologous nucleic acids in C1 metabolizing bacteria is known in the art (see, e.g., U.S. Pat. No. 6,818,424; U.S. Patent Application Publication No. US 2003/0003528). Mu transposon based transformation of methylotrophic bacteria has been described (Akhverdyan et al., *Appl. Microbiol. Biotechnol*. 91:857, 2011). A mini-Tn7 transposon system for single and multicopy expression of heterologous genes without insertional inactivation of host genes in *Methylobacterium* has been described (U.S. Patent Application Publication No. US 2008/0026005).

Various methods for inactivating, knocking-out, or deleting endogenous gene function in $C_1$ metabolizing bacteria may be used. Allelic exchange using suicide vectors to construct deletion/insertional mutants in slow growing $C_1$ metabolizing bacteria have also been described in Toyama and Lidstrom, *Microbiol*. 144:183, 1998; Stolyar et al., *Microbiol*. 145:1235, 1999; Ali et al., *Microbiol*. 152:2931, 2006; Van Dien et al., *Microbiol*. 149:601, 2003.

Suitable homologous or heterologous promoters for high expression of exogenous nucleic acids may be utilized. For example, U.S. Pat. No. 7,098,005 describes the use of promoters that are highly expressed in the presence of methane or methanol for heterologous gene expression in $C_1$ metabolizing bacteria. Additional promoters that may be used include deoxy-xylulose phosphate synthase methanol dehydrogenase operon promoter (Springer et al., *FEMS Microbiol. Lett*. 160:119, 1998); the promoter for PHA synthesis (Foellner et al., *Appl. Microbiol. Biotechnol*. 40:284, 1993); or promoters identified from a native plasmid in methylotrophs (European Patent No. EP 296484). Non-native promoters include the lac operon Plac promoter (Toyama et al., *Microbiol*. 143:595, 1997) or a hybrid promoter such as Ptrc (Brosius et al., *Gene* 27:161, 1984). In certain embodiments, promoters or codon optimization are used for high constitutive expression of exogenous nucleic acids encoding glycerol utilization pathway enzymes in host methanotrophic bacteria. Regulated expression of an exogenous nucleic acid in the host methanotrophic bacterium may also be utilized. In particular, regulated expression of exogenous nucleic acids encoding glycerol utilization enzymes may be desirable to optimize growth rate of the non-naturally occurring methanotrophic bacteria. It is possible that in the absence of glycerol (e.g., during growth on methane as a carbon source), for the glycerol utilization pathway to run in reverse, resulting in secretion of glycerol from the bacteria, thereby lowering growth rate. Controlled expression of nucleic acids encoding glycerol utilization pathway enzymes in response to the presence of glycerol may optimize bacterial growth in a variety of carbon source conditions. For example, an inducible/regulatable system of recombinant protein expression in methylotrophic and methanotrophic bacteria, as described in U.S. Patent Application Publication No. US 2010/0221813, may be used. Regulation of glycerol utilization genes in bacteria is well established (Schweizer and Po, *J. Bacteriol*. 178:5215, 1996; Abram et al., *Appl. Environ. Microbiol*. 74:594, 2008; Darbon et al., *Mol. Microbiol*. 43:1039, 2002; Weissenborn et al., *J. Biol. Chem*. 267:6122, 1992). Glycerol utilization regulatory elements may also be introduced or inactivated in host methanotrophic bacteria for desired expression levels of exogenous nucleic acid molecules encoding glycerol utilization pathway enzymes.

Methods of screening are disclosed in Brock, supra. Selection methods for identifying allelic exchange mutants are known in the art (see, e.g., U.S. Patent Appl. Publication No. US 2006/0057726, Stolyar et al., *Microbiol*. 145:1235, 1999; and Ali et al., *Microbiol*. 152:2931, 2006.

Culture Methods

A variety of culture methodologies may be used for recombinant methanotrophic bacteria described herein. For example, methanotrophic bacteria may be grown by batch culture or continuous culture methodologies. In certain embodiments, the cultures are grown in a controlled culture unit, such as a fermentor, bioreactor, hollow fiber membrane bioreactor, or the like.

A classical batch culturing method is a closed system where the composition of the media is set at the beginning of the culture and not subject to external alterations during the culture process. Thus, at the beginning of the culturing process, the media is inoculated with the desired $C_1$ metabolizing microorganism (e.g., methanotroph) and growth or metabolic activity is permitted to occur without adding anything to the system. Typically, however, a "batch" culture is batch with respect to the addition of carbon source and attempts are often made at controlling factors such as pH and oxygen concentration. In batch systems, the metabolite and biomass compositions of the system change constantly up to the time the culture is terminated. Within batch cultures, cells moderate through a static lag phase to a high growth logarithmic phase and finally to a stationary phase where growth rate is diminished or halted. If untreated, cells in the stationary phase will eventually die. Cells in logarithmic growth phase are often responsible for the bulk production of end product or intermediate in some systems. Stationary or post-exponential phase production can be obtained in other systems.

The Fed-Batch system is a variation on the standard batch system. Fed-Batch culture processes comprise a typical batch system with the modification that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measureable factors, such as pH, dissolved oxygen, and the partial pressure of waste gases such as $CO_2$. Batch and Fed-Batch culturing methods are common and known in the art (see, e.g., Thomas D. Brock, Biotechnology: A Textbook of Industrial Microbiology, $2^{nd}$ Ed. (1989) Sinauer Associates, Inc., Sunderland, Mass.; Deshpande, *Appl. Biochem. Biotechnol.* 36:227, 1992).

Continuous cultures are "open" systems where a defined culture media is added continuously to a bioreactor and an equal amount of conditioned media is removed simultaneously for processing. Continuous cultures generally maintain the cells at a constant high liquid phase density where cells are primarily in logarithmic phase growth. Alternatively, continuous culture may be practiced with immobilized cells where carbon and nutrients are continuously added and valuable products, by-products, and waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limited nutrient, such as the carbon source or nitrogen level, at a fixed rate and allow all other parameters to modulate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art, and a variety of methods are detailed by Brock, supra.

Fatty Acid Derivative Compositions

By way of background, stable isotopic measurements and mass balance approaches are widely used to evaluate global sources and sinks of methane (see Whiticar and Faber, *Org. Geochem.* 10:759, 1986; Whiticar, *Org. Geochem.* 16: 531, 1990). To use $\delta^{13}C$ values of residual methane to determine the amount oxidized, it is necessary to know the degree of isotopic fractionation caused by microbial oxidation of methane. For example, aerobic methanotrophs can metabolize methane through a specific enzyme, methane monooxygenase (MMO). Methanotrophs convert methane to methanol and subsequently formaldehyde. Formaldehyde can be further oxidized to $CO_2$ to provide energy to the cell in the form of reducing equivalents (NADH), or incorporated into biomass through either the RuMP or Serine cycles (Hanson and Hanson, *Microbiol. Rev.* 60:439, 1996), which are directly analogous to carbon assimilation pathways in photosynthetic organisms.

Figure 7:
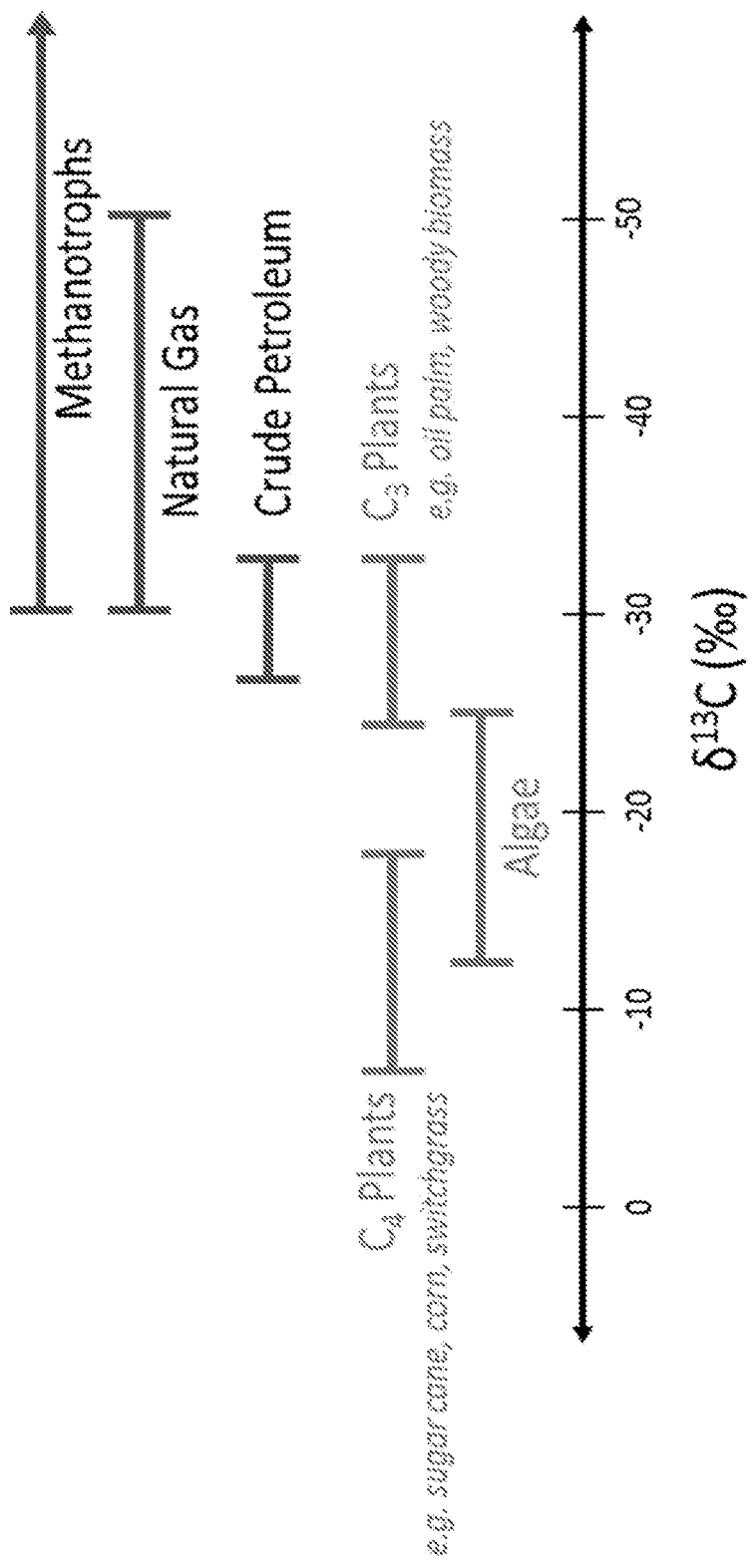
FIG. 7 shows a schematic of the $\delta^{13}C$ distribution of various carbon sources.

More specifically, a Type I methanotroph uses the RuMP pathway for biomass synthesis and generates biomass entirely from $CH_4$, whereas a Type II methanotroph uses the serine pathway that assimilates 50-70% of the cell carbon from $CH_4$ and 30-50% from $CO_2$ (Hanson and Hanson, 1996). Methods for measuring carbon isotope compositions are provided in, for example, Templeton et al. (*Geochim. Cosmochim. Acta* 70:1739, 2006), which methods are hereby incorporated by reference in their entirety. The $^{13}C/^{12}C$ stable carbon ratio of an oil composition from a biomass (provided as a "delta" value ‰, $\delta^{13}C$) can vary depending on the source and purity of the $C_1$ substrate used (see, e.g., FIG. 7).

Fatty acid derivative compositions produced using a $C_1$ metabolizing non-photosynthetic microorganisms and methods described herein, may be distinguished from fatty acids produced from petrochemicals or from photosynthetic microorganisms or plants by carbon fingerprinting. In certain embodiments, compositions of $C_8$ to $C_{24}$ fatty aldehyde, fatty alcohol, fatty ester wax, hydroxy fatty acid, dicarboxylic acid, or any combination thereof have a $\delta^{13}C$ of less than −30‰, less than −31‰, less than −32‰, less than −33‰, less than −34‰, less than −35‰, less than −36‰, less than −37‰, less than −38‰, less than −39‰, less than −40‰, less than −41‰, less than −42‰, less than −43‰, less than −44‰, less than −45‰, less than −46‰, less than −47‰, less than −48‰, less than −49‰, less than −50‰, less than −51‰, less than −52‰, less than −53‰, less than −54‰, less than −55‰, less than −56‰, less than −57‰, less than −58‰, less than −59‰, less than −60‰, less than −61‰, less than −62‰, less than −63‰, less than −64‰, less than −65‰, less than −66‰, less than −67‰, less than −68‰, less than −69‰, or less than −70‰.

In some embodiments, a $C_1$ metabolizing microorganism biomass comprises a fatty acid derivative composition as described herein, wherein the fatty acid derivative containing biomass or a fatty acid derivative composition has a $\delta^{13}C$ of about −35‰ to about −50‰, −45‰ to about −35‰, or about −50‰ to about −40‰, or about −45‰ to about −65‰, or about −60‰ to about −70‰, or about −30‰ to about −70‰. In certain embodiments, a fatty acid derivative composition comprises at least 50% fatty acids or comprises at least 50% fatty acid derivatives. In further embodiments, a fatty acid derivative composition comprises fatty aldehyde, fatty alcohol, fatty ester wax, hydroxy fatty acid, dicarboxylic acid, or any combination thereof. In still further embodiments, a fatty acid derivative composition comprises $C_8$-$C_{24}$ fatty alcohol, $C_8$-$C_{24}$ branched chain fatty alcohol, $C_8$-$C_{24}$ fatty aldehyde, $C_8$-$C_{24}$ ω-hydroxy fatty acid, or $C_8$-$C_{24}$ dicarboxylic acid alcohol. In yet further embodiments, a fatty acid derivative composition comprises a majority (more than 50% w/w) of fatty acids having carbon chain lengths ranging from $C_8$ to $C_{14}$ or from $C_{10}$ to $C_{16}$ or from $C_{14}$ to $C_{24}$, or a majority of fatty acid derivatives having carbon chain lengths of less than $C_{18}$, or a fatty alcohol containing composition wherein at least 70% of the total fatty alcohol comprises $C_{10}$ to $C_{18}$ fatty alcohol.

In further embodiments, a $C_1$ metabolizing non-photosynthetic microorganism fatty acid derivative containing biomass or a fatty acid derivative composition has a $\delta^{13}C$ of less than about −30‰, or ranges from about −40‰ to about −60‰. In certain embodiments, the fatty acid derivative containing biomass comprises a recombinant $C_1$ metabolizing non-photosynthetic microorganism together with the spent media, or the fatty acid derivative containing biomass comprises a spent media supernatant composition from a culture of a recombinant $C_1$ metabolizing non-photosynthetic microorganism, wherein the $\delta^{13}C$ of the fatty acid derivative containing biomass or a fatty acid derivative composition obtained therefrom is less than about −30‰. In certain other embodiments, a fatty acid derivative composition is isolated, extracted or concentrated from a fatty acid derivative containing biomass, which can comprise recombinant $C_1$ metabolizing non-photosynthetic microorganisms together with the spent media from a culture, or a spent media supernatant composition from a culture of a recombinant $C_1$ metabolizing non-photosynthetic microorganism.

In certain embodiments, fatty acid derivative containing biomass or a fatty acid derivative composition is of a recombinant $C_1$ metabolizing non-photosynthetic microorganism comprises a heterologous polynucleotide encoding a fatty acid converting enzyme. In further embodiments, such a heterologous polynucleotide encodes a fatty acyl-CoA reductase, carboxylic acid reductase, thioesterase, acyl-CoA synthetase, P450, monoxygenase, or any combination thereof. In further embodiments, fatty acid derivative containing biomass or a fatty acid derivative composition is of a recombinant $C_1$ metabolizing non-photosynthetic microorganism comprising a heterologous nucleic acid sequence as described herein that is codon optimized for efficient expression in a $C_1$ metabolizing non-photosynthetic microorganism.

Exemplary organisms for use in generating fatty acid derivative containing biomass or a fatty acid derivative composition is of a recombinant $C_1$ metabolizing non-photosynthetic microorganisms of this disclosure include bacteria or yeast. In certain embodiments, fatty acid derivative containing biomass or a fatty acid derivative composition is of a $C_1$ metabolizing bacteria from a methanotroph or methylotroph, such as a *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* Y (NRRL B-11,201), *Methylococcus capsulatus* Bath (NCIMB 11132), *Methylobacterium organophilum* (ATCC 27,886), *Methylomonas* sp. AJ-3670 (FERM P-2400), *Methylomicrobium alcaliphilum*, *Methylocella silvestris*, *Methylacidiphilum infernorum*, *Methylibium petroleiphilum*, *Methylobacterium extorquens*, *Methylobacterium radiotolerans*, *Methylobacterium populi*, *Methylobacterium chloromethanicum*, *Methylobacterium nodulans*, or any combination thereof.

In further embodiments, a fatty acid derivative containing biomass or a fatty acid derivative composition is of a $C_1$ metabolizing bacteria from a recombinant $C_1$ metabolizing bacteria of this disclosure is a syngas metabolizing bacteria, such as *Clostridium autoethanogenum*, *Clostridium ljungdahli*, *Clostridium ragsdalei*, *Clostridium carboxydivorans*, *Butyribacterium methylotrophicum*, *Clostridium woodii*, *Clostridium neopropanologen*, or a combination thereof.

EXAMPLES

Example 1

Lipid Extraction from $C_1$ Metabolizing Microorganisms

A fatty acid oil composition contained within a harvested bacterial biomass was extracted using a modified version of Folch's extraction protocol (Folch et al., *J. Biol. Chem.* 226:497, 1957), performed at 20° C. (i.e., room temperature) and in an extraction solution made up of one volume methanol in two volumes chloroform (CM solution). About 5 g wet cell weight (WCW) of either fresh bacterial biomass (or bacterial biomass stored at −80° C. and subsequently thawed) was used for extractions. A 100 mL CM solution was added to the cell material and the mixture was extracted vigorously in a separatory funnel. After at least 10 minutes, three phases were resolved. The organic phase containing extracted lipids settled at the bottom of the separatory funnel, which was drained into a clean glass bottle. The middle layer contained primarily lysed cellular materials and could be separated from the light water phase containing salts and other soluble cellular components.

Optionally, solids in the water phase can be concentrated using a centrifuge or other mechanical concentration equipment. The water removed from the solids may be recycled, while the solids, with some residual water, can be fed to a solids processing unit.

To enhance the lipid extraction efficiency, a second extraction step was carried out by adding an additional 100 mL fresh CM solution directly into the separatory funnel containing the remaining lysed cell mass and residual water. The mixture was again mixed thoroughly, the phases allowed to separate, and the bottom organic phases from the two extractions were pooled. The pooled organic phases were then washed with 100 mL deionized water in a separatory funnel to remove any residual water-soluble material. The separated organic fraction was again isolated from the bottom of the separatory funnel and solvent was removed by rotary evaporation with heat, preferably in the absence of oxygen, or by evaporation at 55° C. under a stream of nitrogen.

TABLE 1

Extracted Lipid Content from Three Different Methanotrophs

| Batch No. | Reference Strain | Lipid Fraction (g/g DCW)* |
|---|---|---|
| 68C | *Methylosinus trichosporium* OB3b | 40.1 |
| 62A | *Methylococcus capsulatus* Bath | 10.3 |
| 66A | *Methylomonas* sp. 16a | 9.3 |

*Grams of extracted material per gram of dry cell weight (DCW)

The solidified fatty acid compositions extracted from the harvested cultures of *M. trichosporium* OB3b, *Methylococcus capsulatus* Bath, and *Methylomonas* sp. 16a were each weighed and are shown as the weight fraction of the original dry cell weight (DCW) in Table 1. These data show that a significant fraction of the DCW from these $C_1$ metabolizing microorganisms is made up of lipids.

The fatty acid composition from *Methylomonas* sp. 16a biomass was also extracted using hexane:isopropanol (HIP) extraction method of Hara and Radin (*Anal. Biochem.* 90:420, 1978). Analysis of the fatty acid composition extracted using the HIP method showed that the fatty acid composition was essentially identical to the fatty acid composition extracted using the modified Folch method (data not shown).

Example 2

Fatty Acid Methyl Ester Conversion of Lipids from $C_1$ Metabolizing Microorganisms The lipid fractions extracted from *M. capsulatus* Bath, *M. trichosporium* OB3b, and *Methylomonas* sp. 16a culture biomass in the form of dry solids were individually hydrolyzed with potassium hydroxide (KOH) and converted into fatty acid methyl esters (FAMEs) via reaction with methanol in a single step. About 5 g of extracted solid lipids in a 10 mL glass bottle were dissolved with 5 mL of 0.2 M KOH solution of toluene:methanol (1:1 v/v). The bottle was agitated vigorously and then mixed at 250 rpm at 42° C. for 60 minutes, after which the solution was allowed to cool to ambient temperature and transferred to a separatory funnel. Approximately 5 mL distilled water and 5 mL CM solution were added to the separatory funnel, mixed, and then the phases were allowed to separate by gravity or by centrifugation (3,000 rpm, 25° C.) for 5 minutes. The top aqueous layer was removed, which contains dissolved glycerol phosphate esters, while the heavy oil phase (bottom) was collected and concentrated to dryness by rotary evaporation or by a constant nitrogen stream.

Analysis of FFAs and FAMEs found in lipids from each methanotroph culture was performed using a gas chromatograph/mass spectrometer (GC/MS). The solids collected before and after the hydrolysis/transesterification step were dissolved in 300 μL butyl acetate containing undecanoic acid as an internal standard for GC/MS analysis. The resulting solution was centrifuged for 5 minutes at 14,000 rpm to remove insoluble residues. The same volume equivalent of N,O-Bis(trimethylsilyl)trifluoroacetamide was added to the supernatant from the centrifugation step and vortexed briefly. Samples were loaded on an GC equipped with mass spectrometer detector (HP 5792), and an Agilent HP-5MS GC/MS column (30.0 m×250 μm×0.25 μm film thickness) was used to separate the FFAs and FAMEs. Identity of FFAs and FAMEs was confirmed with retention time and electron ionization of mass spectra of their standards. The GC/MS method utilized helium as the carrier gas at a flow of 1.2 mL/min. The injection port was held at 250° C. with a split ratio of 20:1. The oven temperature was held at 60° C. for 1 minute followed by a temperature gradient comprising an 8° C. increase/min until 300° C. The % area of each FFA and FAME was calculated based on total ions from the mass detector response.

The solid residue collected before and after hydrolysis/transesterification were analyzed for FFAs and FAMEs by GC/MS (see Table 2).

TABLE 2

Relative composition of FFA and FAME in Extracted Lipids Before and After KOH Hydrolysis/Esterification

| Fatty Acid Type | *M. capsulatus* Bath | | *M. trichosporium* OB3b | | *Methylomonas* sp. 16a | |
|---|---|---|---|---|---|---|
| | With hydro- lysis % Area | Without hydro- lysis % Area | With hydro- lysis % Area | Without hydro- lysis % Area | With hydro- lysis % Area | Without hydro- lysis % Area |
| C14:0 FFA | — | — | — | — | — | 12.9 |
| C16:0 FFA | 0.5 | 84.1 | — | 43.7 | — | 8.1 |
| C16:1 FFA | — | 13.4 | — | — | — | 76.1 |
| C18:0 FFA | 0.4 | 2.5 | — | 31.2 | — | 1.3 |
| C18:1 FFA | — | — | — | 25.1 | — | 1.5 |
| C14:0 FAME | 3.4 | — | — | — | 7.2 | — |
| C16:0 FAME | 54.4 | — | 1.4 | — | 14.7 | — |
| C16:1 FAME | 41.3 | — | 6.8 | — | 61.3 | — |
| C18:0 FAME | — | — | 1.0 | — | N.D. | — |
| C18:1 FAME | — | — | 90.8 | — | 16.8 | — |

\* — = Not detectable; % Area: MS detector response-Total ions

As is evident from Table 2, extracted lipid compositions before hydrolysis/transesterification have abundant free fatty acids and additional fatty acids present, but the FFAs are converted into fatty acid methyl esters of various lengths after hydrolysis/transesterification. These data indicate that oil compositions from the $C_1$ metabolizing microorganisms of this disclosure can be refined and used to make high-value molecules.

Example 3

Stable Carbon Isotope Distribution in Lipids from $C_1$ Metabolizing Microorganisms Dry samples of *M. trichosporium* biomass and lipid fractions were analyzed for carbon and nitrogen content (% dry weight), and carbon ($^{13}C$) and nitrogen ($^{15}N$) stable isotope ratios via elemental analyzer/continuous flow isotope ratio mass spectrometry using a CHNOS Elemental Analyzer (vario ISOTOPE cube, Elementar, Hanau, Germany) coupled with an IsoPrime100 IRMS (Isoprime, Cheadle, UK). Samples of methanotrophic biomass cultured in fermenters or serum bottles were centrifuged, resuspended in deionized water and volumes corresponding to 0.2-2 mg carbon (about 0.5-5 mg dry cell weight) were transferred to 5×9 mm tin capsules (Costech Analytical Technologies, Inc., Valencia, Calif.) and dried at 80° C. for 24 hours. Similarly, previously extracted lipid fractions were suspended in chloroform and volumes containing 0.1-1.5 mg carbon were transferred to tin capsules and evaporated to dryness at 80° C. for 24 hours. Standards containing 0.1 mg carbon provided reliable $\delta^{13}C$ values.

The isotope ratio is expressed in "delta" notation (‰), wherein the isotopic composition of a material relative to that of a standard on a per million deviation basis is given by $\delta^{13}C$ (or $\delta^{15}N$)=$(R_{Sample}/R_{Standard-1})\times 1{,}000$, wherein R is the molecular ratio of heavy to light isotope forms. The standard for carbon is the Vienna Pee Dee Belemnite (V-PDB) and for nitrogen is air. The NIST (National Institute of Standards and Technology) proposed SRM (Standard Reference Material) No. 1547, peach leaves, was used as a calibration standard. All isotope analyses were conducted at the Center for Stable Isotope Biogeochemistry at the University of California, Berkeley. Long-term external precision for C and N isotope analyses is 0.10‰ and 0.15‰, respectively.

*M. trichosporium* strain OB3b was grown on methane in three different fermentation batches, *M. capsulatus* Bath was grown on methane in two different fermentation batches, and *Methylomonas* sp. 16a was grown on methane in a single fermentation batch. The biomass from each of these cultures was analyzed for stable carbon isotope distribution ($\delta^{13}C$ values; see Table 3).

TABLE 3

Stable Carbon Isotope Distribution in Different Methanotrophs

| Methanotroph | Batch No. | EFT (h)† | $OD_{600}$ | DCW* | $\delta^{13}C$ Cells |
|---|---|---|---|---|---|
| Mt OB3b | 68A | 48 | 1.80 | 1.00 | −57.9 |
| | | 64 | 1.97 | 1.10 | −57.8 |
| | | 71 | 2.10 | 1.17 | −58.0 |
| | | 88 | 3.10 | 1.73 | −58.1 |
| | | 97 | 4.30 | 2.40 | −57.8 |
| | | 113 | 6.00 | 3.35 | −57.0 |
| | | 127 | 8.40 | 4.69 | −56.3 |
| Mt OB3b | 68B | 32 | 2.90 | 1.62 | −58.3 |
| | | 41 | 4.60 | 2.57 | −58.4 |
| | | 47 | 5.89 | 3.29 | −58.0 |
| | | 56 | 7.90 | 4.41 | −57.5 |
| Mt OB3b | 68C | 72 | 5.32 | 2.97 | −57.9 |
| | | 79.5 | 5.90 | 3.29 | −58.0 |
| | | 88 | 5.60 | 3.12 | −57.8 |
| | | 94 | 5.62 | 3.14 | −57.7 |
| Mc Bath | 62B | 10 | 2.47 | 0.88 | −59.9 |
| | | 17.5 | 5.80 | 2.06 | −61.0 |
| | | 20 | 7.32 | 2.60 | −61.1 |
| | | 23 | 9.34 | 3.32 | −60.8 |
| | | 26 | 10.30 | 3.66 | −60.1 |
| Mc Bath | 62A | 10 | 2.95 | 1.05 | −55.9 |
| | | 13.5 | 3.59 | 1.27 | −56.8 |
| | | 17.5 | 5.40 | 1.92 | −55.2 |
| | | 23 | 6.08 | 2.16 | −57.2 |
| | | 26 | 6.26 | 2.22 | −57.6 |
| Mms 16a | 66B | 16 | 2.13 | 0.89 | −65.5 |
| | | 18 | 2.59 | 1.09 | −65.1 |
| | | 20.3 | 3.62 | 1.52 | −65.5 |
| | | 27 | 5.50 | 2.31 | −66.2 |
| | | 40.5 | 9.80 | 4.12 | −66.3 |

*DCW, Dry Cell Weight is reported in g/L calculated from the measured optical densities ($OD_{600}$) using specific correlation factors relating OD of 1.0 to 0.558 g/L for Mt OB3b, OD of 1.0 to 0.355 g/L for Mc Bath, and OD of 1.0 to 0.42 g/L for Mms 16a. For Mt OB3b, the initial concentration of bicarbonate used per fermentation was 1.2 mM or 0.01% (Batch No. 68C) and 0.1% or 12 mM (Batch Nos. 68A and 68B).
†EFT = effective fermentation time in hours In addition, stable carbon isotope analysis was performed for biomass and corresponding lipid fractions (see Table 4) from strains *Methylosinus trichosporium* OB3b (Mt OB3b), *Methylococcus capsulatus* Bath (Mc Bath), and *Methylomonas* sp. 16a (Mms 16a) grown on methane in bioreactors.

TABLE 4

Stable Carbon Isotope Distribution in Cells and Lipids

| Batch No. | Strain | $\delta^{13}C$ Cells | $\delta^{13}C$ Lipids |
|---|---|---|---|
| 68C | Mt OB3b | −57.7 | −48.6 |
| 62A | Mc Bath | −57.6 | −52.8 |
| 66A | Mms 16a | −64.4 | −42.2 |

Biomass from strains Mt OB3b, Mc Bath and Mms 16a were harvested at 94 h (3.14 g DCW/L), 26 h (2.2 g DCW/L) and 39 h (1.14 g DCW/L), respectively. The $\delta^{13}C$ values for lipids in Table 4 represent an average of duplicate determinations.

Example 4

Effect of Methane Source and Purity on Stable Carbon Isotope Distribution in Lipids To examine methanotroph growth on methane containing natural gas components, a series of 0.5-liter serum bottles containing 100 mL defined media MMS1.0 were inoculated with *Methylosinus trichosporium* OB3b or *Methylococcus capsulatus* Bath from a serum bottle batch culture (5% v/v) grown in the same media supplied with a 1:1 (v/v) mixture of methane and air. The composition of medium MMS1.0 was as follows: 0.8 mM $MgSO_4*7H_2O$, 30 mM $NaNO_3$, 0.14 mM $CaCl_2$, 1.2 mM $NaHCO_3$, 2.35 mM $KH_2PO_4$, 3.4 mM $K_2HPO_4$, 20.7 μM $Na_2MoO_4*2H_2O$, 6 μM $CuSO_4*5H_2O$, 10 μM $Fe^{III}$—Na-EDTA, and 1 mL per liter of a trace metals solution (containing, per L: 500 mg $FeSO4*7H_2O$, 400 mg $ZnSO_4*7H_2O$, 20 mg $MnCl_2*7H2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$-Na-EDTA were added after media was autoclaved and cooled. The final pH of the media was 7.0±0.1.

The inoculated bottles were sealed with rubber sleeve stoppers and injected with 60 mL methane gas added via syringe through sterile 0.45 μm filter and sterile 27G needles. Duplicate cultures were each injected with 60 mL volumes of (A) methane of 99% purity (grade 2.0, Praxair through Alliance Gas, San Carlos, Calif.), (B) methane of 70% purity representing a natural gas standard (Sigma-Aldrich; also containing 9% ethane, 6% propane, 3% methylpropane, 3% butane, and other minor hydrocarbon components), (C) methane of 85% purity delivered as a 1:1 mixture of methane sources A and B; and (D) >93% methane (grade 1.3, Specialty Chemical Products, South Houston, Tex.; in-house analysis showed composition >99% methane). The cultures were incubated at 30° C. (*M. trichosporium* strain OB3b) or 42° C. (*M. capsulatus* Bath) with rotary shaking at 250 rpm and growth was measured at approximately 12 hour intervals by withdrawing 1 mL samples to determine $OD_{600}$. At these times, the bottles were vented and headspace replaced with 60 mL of the respective methane source (A, B, C, or D) and 60 mL of concentrated oxygen (at least 85% purity). At about 24 hour intervals, 5 mL samples were removed, cells recovered by centrifugation (8,000 rpm, 10 minutes), and then stored at −80° C. before analysis.

Analysis of carbon and nitrogen content (% dry weight), and carbon ($^{13}C$) and nitrogen ($^{15}N$) stable isotope ratios, for methanotrophic biomass derived from *M. trichosporium* strain OB3b and *M. capsulatus* Bath were carried out as described in Example 3. Table 5 shows the results of stable carbon isotope analysis for biomass samples from *M. capsulatus* Bath grown on methane having different levels of purity and in various batches of bottle cultures.

TABLE 5

Stable Carbon Isotope Distribution of *M. capsulatus* Bath Grown on Different Methane Sources having Different Purity

| Methane* | Batch No. | Time (h)† | $OD_{600}$ | DCW (g/L) | $\delta^{13}C$ Cells |
|---|---|---|---|---|---|
| A | 62C | 22 | 1.02 | 0.36 | −40.3 |
| | | 56 | 2.01 | 0.71 | −41.7 |
| | | 73 | 2.31 | 0.82 | −42.5 |
| | 62D | 22 | 1.14 | 0.40 | −39.3 |
| | | 56 | 2.07 | 0.73 | −41.6 |
| | | 73 | 2.39 | 0.85 | −42.0 |

TABLE 5-continued

Stable Carbon Isotope Distribution of M. capsulatus Bath Grown on Different Methane Sources having Different Purity

| Methane* | Batch No. | Time (h)† | OD$_{600}$ | DCW (g/L) | $\delta^{13}$C Cells |
|---|---|---|---|---|---|
| B | 62E | 22 | 0.47 | 0.17 | −44.7 |
| | | 56 | 0.49 | 0.17 | −45.4 |
| | | 73 | 0.29 | 0.10 | −45.4 |
| | 62F | 22 | 0.62 | 0.22 | −42.3 |
| | | 56 | 0.63 | 0.22 | −43.6 |
| | | 73 | 0.30 | 0.11 | −43.7 |
| C | 62G | 22 | 0.70 | 0.25 | −40.7 |
| | | 56 | 1.14 | 0.40 | −44.8 |
| | | 73 | 1.36 | 0.48 | −45.8 |
| | 62H | 22 | 0.62 | 0.22 | −40.9 |
| | | 56 | 1.03 | 0.37 | −44.7 |
| | | 73 | 1.23 | 0.44 | −45.9 |

*Methane purity: A: 99% methane, grade 2.0 (min. 99%); B: 70% methane, natural gas standard (contains 9% ethane, 6% propane, 3% methylpropane, 3% butane); C: 85% methane (1:1 mix of A and B methane)
†Time = bottle culture time in hours The average $\delta^{13}$C for *M. capsulatus* Bath grown on one source of methane (A, 99%) was −41.2±1.2, while the average $\delta^{13}$C for *M. capsulatus* Bath grown on a different source of methane (B, 70%) was −44.2±1.2. When methane sources A and B were mixed, an intermediate average $\delta^{13}$C of −43.8±2.4 was observed. These data show that the $\delta^{13}$C of cell material grown on methane sources A and B are significantly different from each other due to the differences in the $\delta^{13}$C of the input methane. But, cells grown on a mixture of the two gasses preferentially utilize $^{12}$C and, therefore, show a trend to more negative $\delta^{13}$C values.

A similar experiment was performed to examine whether two different methanotrophs, *Methylococcus capsulatus* Bath and *Methylosinus trichosporium* OB3b, grown on different methane sources and in various batches of bottle cultures showed a difference in $\delta^{13}$C distribution (see Table 6).

TABLE 6

Stable Carbon Isotope Distribution of Different Methanotrophs Grown on Different Methane Sources of Different Purity

| Strain | Methane* | Batch No. | Time (h)† | OD$_{600}$ | DCW (g/L) | $\delta^{13}$C Cells |
|---|---|---|---|---|---|---|
| Mc Bath | A | 62I | 18 | 0.494 | 0.18 | −54.3 |
| | | | 40 | 2.33 | 0.83 | −42.1 |
| | | | 48 | 3.08 | 1.09 | −37.1 |
| Mc Bath | D | 62J | 18 | 0.592 | 0.21 | −38.3 |
| | | | 40 | 1.93 | 0.69 | −37.8 |
| | | | 48 | 2.5 | 0.89 | −37.8 |
| Mc Bath | D | 62K | 18 | 0.564 | 0.20 | −38.6 |
| | | | 40 | 1.53 | 0.54 | −37.5 |
| | | | 48 | 2.19 | 0.78 | −37.6 |
| Mt OB3b | A | 68D | 118 | 0.422 | 0.24 | −50.2 |
| | | | 137 | 0.99 | 0.55 | −47.7 |
| | | | 162 | 1.43 | 0.80 | −45.9 |
| Mt OB3b | A | 68E | 118 | 0.474 | 0.26 | −49.9 |
| | | | 137 | 1.065 | 0.59 | −47.6 |
| | | | 162 | 1.51 | 0.84 | −45.2 |
| Mt OB3b | D | 68F | 118 | 0.534 | 0.30 | −45.6 |
| | | | 137 | 1.119 | 0.62 | −38.7 |
| | | | 162 | 1.63 | 0.91 | −36.4 |
| Mt OB3b | D | 68G | 118 | 0.544 | 0.30 | −44.8 |
| | | | 137 | 1.131 | 0.63 | −39.1 |
| | | | 162 | 1.6 | 0.89 | −34.2 |

*Methane sources and purity: A: 99% methane (grade 2.0); D: >93% methane (grade 1.3)
†Time = bottle culture time in hours The average $\delta^{13}$C for *M. capsulatus* grown on a first methane source (A) was −44.5±8.8, while the average $\delta^{13}$C for *M. trichosporium* was −47.8±2.0 grown on the same methane source. The average $\delta^{13}$C for *M. capsulatus* grown on the second methane source (B) was −37.9±0.4, while the average $\delta^{13}$C for *M. trichosporium* was −39.8±4.5. These data show that the $\delta^{13}$C of cell material grown on a methane source is highly similar to the $\delta^{13}$C of cell material from a different strain grown on the same source of methane. Thus, the observed $\delta^{13}$C of cell material appears to be primarily dependent on the composition of the input gas rather than a property of a particular bacterial strain being studied.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. provisional patent application Ser. No. 61/724,733, filed Nov. 9, 2012, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A alpha-proteobacterial methanotroph, comprising a heterologous nucleic acid molecule encoding a fatty acid converting enzyme, wherein the alpha-proteobacterial methanotroph comprising the heterologous nucleic acid molecule encoding the fatty acid converting enzyme is capable of converting a $C_1$ substrate into a $C_8$-$C_{24}$ fatty aldehyde, fatty alcohol, fatty ester wax, a hydroxy fatty acid, dicarboxylic acid, or a combination thereof, and wherein the encoded fatty acid converting enzyme comprises:
   (a) a fatty acyl-CoA reductase capable of forming a fatty alcohol; or
   (b) a fatty acyl-CoA reductase capable of forming a fatty aldehyde; or
   (c) a carboxylic acid reductase; and
   (d) a thioesterase; and/or
   (e) an acyl-CoA synthetase.

2. The alpha-proteobacterial methanotroph according to claim 1, wherein the host alpha-proteobacterial methanotroph is selected from *Methylosinus trichosporium, Methylosinus sporium, Methylocystis parvus, Methylobacterium organophilum, Methylocella silvestris, Methylocella palustris, Methylocella tundrae, Methylocella daltona, Methylocystis bryophila, Methylocapsa aurea*, or high growth variants thereof.

3. The alpha-proteobacterial methanotroph according to claim 1, wherein the $C_1$ substrate is methane, natural gas, or unconventional natural gas.

4. The alpha-proteobacterial methanotroph according to claim 1, wherein:
   (a) the fatty acyl-CoA reductase capable of forming a fatty alcohol is FAR, CER4, or Maqu_2220; or
   (b) the fatty acyl-CoA reductase capable of forming a fatty aldehyde is acr1.

5. The alpha-proteobacterial methanotroph according to claim 4, wherein:
   (a) the thioesterase is a tesA lacking a signal peptide, UcFatB or BTE; and/or
   (b) the acyl-CoA synthetase is a FadD, yng1, or FAA2.

6. The alpha-proteobacterial methanotroph according to claim 5, wherein:
   (a) endogenous thioesterase activity is reduced, minimal or abolished as compared to unaltered endogenous thioesterase activity; and/or
   (b) endogenous acyl-CoA synthetase activity is reduced, minimal or abolished as compared to unaltered endogenous acyl-CoA synthetase activity.

7. The alpha-proteobacterial methanotroph according to claim 5, wherein the alpha-proteobacterial methanotroph further comprises a heterologous nucleic acid molecule encoding a P450 enzyme or monoxygenase enzyme to produce ω-hydroxy fatty acid.

8. The alpha-proteobacterial methanotroph according to claim 7, wherein endogenous alcohol dehydrogenase activity is inhibited as compared to unaltered endogenous alcohol dehydrogenase activity.

9. The alpha-proteobacterial methanotroph according to claim 5, wherein endogenous alcohol dehydrogenase activity is increased or elevated as compared to unaltered endogenous alcohol dehydrogenase activity to produce dicarboxylic acid.

10. The alpha-proteobacterial methanotroph according to claim 5, wherein the alpha-proteobacterial methanotroph produces fatty alcohol comprising:
    (a) one or more of $C_8$-$C_{14}$ or $C_{10}$-$C_{16}$ or $C_{14}$-$C_{24}$ fatty alcohols;
    (b) $C_{10}$ to $C_{18}$ fatty alcohol and the $C_{10}$ to $C_{18}$ fatty alcohols comprise at least 70% of the total fatty alcohol; or
    (c) a branched chain fatty alcohol.

11. The alpha-proteobacterial methanotroph according to claim 1, comprising:
    (a) a heterologous nucleic acid molecule encoding an acyl-CoA independent fatty acyl-CoA reductase, and a heterologous nucleic acid molecule encoding a thioesterase, wherein the methanotroph is capable of converting a $C_1$ substrate into a $C_8$-$C_{24}$ fatty alcohol;
    (b) a heterologous nucleic acid molecule encoding an acyl-CoA dependent fatty acyl-CoA reductase, a heterologous nucleic acid molecule encoding a thioesterase, and a heterologous nucleic acid molecule encoding an acyl-CoA synthetase, wherein the methanotroph is capable of converting a $C_1$ substrate into a $C_8$-$C_{24}$ fatty alcohol;
    (c) a heterologous nucleic acid molecule encoding a carboxylic acid reductase, a heterologous nucleic acid molecule encoding a phosphopantetheinyl tranferase, and a heterologous nucleic acid molecule encoding an alcohol dehydrogenase, wherein the methanotroph is capable of converting a $C_1$ substrate into a $C_8$-$C_{24}$ fatty alcohol;
    (d) a heterologous nucleic acid molecule encoding a fatty acyl-CoA reductase, a heterologous nucleic acid molecule encoding a thioesterase, and a heterologous nucleic acid molecule encoding a P450 or monooxygenase, wherein the native alcohol dehydrogenase is inhibited, and wherein the methanotroph is capable of converting a $C_1$ substrate into a $C_8$-$C_{24}$ ω-hydroxy fatty acid; or
    (e) a heterologous nucleic acid molecule encoding a fatty acyl-CoA reductase, and a heterologous nucleic acid molecule encoding a thioesterase, wherein the methanotroph over-expresses native alcohol dehydrogenase as compared to the normal expression level of native alcohol dehydrogenase or comprises a heterologous nucleic acid molecule encoding an alcohol dehydrogenase or both, and wherein the methanotroph is capable of converting a $C_1$ substrate into a $C_8$-$C_{24}$ dicarboxylic acid alcohol.

12. The alpha-proteobacterial methanotroph according to claim 11, wherein the alpha-proteobacterial methanotroph is selected from *Methylosinus trichosporium* OB3b, *Methylosinus sporium*, *Methylocystis parvus*, or a high growth variant thereof.

13. A method for making a fatty acid derivative, comprising culturing a alpha-proteobacterial methanotroph with a $C_1$ substrate feedstock and recovering the fatty acid derivative,
    wherein the alpha-proteobacterial methanotroph comprises a heterologous nucleic acid molecule encoding a fatty acid converting enzyme,
    wherein the alpha-proteobacterial methanotroph converts the $C_1$ substrate into a $C_8$-$C_{24}$ fatty acid derivative comprising a fatty aldehyde, a fatty alcohol, fatty ester wax, a hydroxy fatty acid, a dicarboxylic acid, or a combination thereof, and
    wherein the encoded fatty acid converting enzyme comprises:
    (a) a fatty acyl-CoA reductase capable of forming a fatty alcohol; or
    (b) a fatty acyl-CoA reductase capable of forming a fatty aldehyde; or
    (c) a carboxylic acid reductase; and
    (d) a thioesterase; and/or
    (e) an acyl-CoA synthetase.

14. The method according to claim 13, wherein the alpha-proteobacterial methanotroph is selected from a *Methylosinus trichosporium, Methylosinus sporium, Methylocystis parvus, Methylobacterium organophilum, Methylocella silvestris, Methylocella palustris, Methylocella tundrae, Methylocella daltona, Methylocystis bryophila, Methylocapsa aurea*, or high growth variants thereof.

15. The method according to claim 13, wherein the culture further comprises a heterologous bacterium.

16. The method according to claim 13, wherein:
    (a) the fatty acyl-CoA reductase capable of forming a fatty alcohol is FAR, CER4, or Maqu_2220; or
    (b) the fatty acyl-CoA reductase capable of forming a fatty aldehyde is acr1.

17. The method according to claim 13, wherein the thioesterase is a tesA lacking a signal peptide, UcFatB or BTE.

18. The method according to claim 17, wherein endogenous thioesterase activity is reduced, minimal or abolished as compared to unaltered endogenous thioesterase activity.

19. The method according to claim 16, wherein the acyl-CoA synthetase is FadD, yng1, or FAA2.

20. The method according to claim 16, wherein endogenous acyl-CoA synthetase activity is reduced, minimal or abolished as compared to unaltered endogenous acyl-CoA synthetase activity.

21. The method according to claim 13, further comprising a heterologous nucleic acid molecule encoding a P450 enzyme or monoxygenase enzyme to produce w-hydroxy fatty acid.

22. The method according to claim 21, wherein endogenous alcohol dehydrogenase activity is reduced, minimal or abolished as compared to unaltered endogenous alcohol dehydrogenase activity.

23. The method according to claim 13, wherein endogenous alcohol dehydrogenase activity is increased or elevated as compared to unaltered endogenous alcohol dehydrogenase activity to produce dicarboxylic acid.

24. The method according to claim 13, wherein the alpha-proteobacterial methanotroph produces fatty alcohol comprising one or more of $C_8$-$C_{14}$ or $C_{10}$-$C_{16}$ or $C_{12}$-$C_{14}$ or $C_{14}$-$C_{18}$ or $C_{14}$-$C_{24}$ fatty alcohols.

25. The method according to claim 13, wherein the alpha-proteobacterial methanotroph produces fatty alcohol comprising $C_{10}$ to $C_{18}$ fatty alcohol and the $C_{10}$ to $C_{18}$ fatty alcohols comprise at least 70% of the total fatty alcohol.

26. The method according to claim 13, wherein the alpha-proteobacterial methanotroph produces fatty alcohols comprising a branched chain fatty alcohol.

27. The method according to claim 13, wherein the $C_1$ substrate is methane, natural gas, or unconventional natural gas.

28. The method according to claim 13, wherein the $C_1$ substrate is methane, and the alpha-proteobacterial methanotrophs are cultured under aerobic conditions.

29. The method according to claim 13, wherein the culturing is in a fermentor or bioreactor.

30. An aerobic, facultative methanotrophic bacteria, comprising a heterologous nucleic acid molecule encoding a fatty acid converting enzyme, wherein the facultative methanotrophic bacteria comprising the heterologous nucleic acid molecule encoding the fatty acid converting enzyme is capable of converting a $C_1$ substrate under aerobic conditions into a $C_8$-$C_{24}$ fatty aldehyde, fatty alcohol, fatty ester wax, a hydroxy fatty acid, dicarboxylic acid, or a combination thereof, and wherein the encoded fatty acid converting enzyme comprises:
(a) a fatty acyl-CoA reductase capable of forming a fatty alcohol; or
(b) a fatty acyl-CoA reductase capable of forming a fatty aldehyde; or
(c) a carboxylic acid reductase; and
(d) a thioesterase; and/or
(e) an acyl-CoA synthetase.

31. The facultative methanotrophic bacteria according to claim 30, wherein the host facultative methanotrophic bacteria is selected from *Methylobacterium organophilum, Methylocella silvestris, Methylocella palustris, Methylocella tundrae, Methylocella daltona, Methylocystis bryophila, Methylocapsa aurea*, or high growth variants thereof.

32. A methylotrophic bacteria, comprising a heterologous nucleic acid molecule encoding a fatty acid converting enzyme, wherein the methylotrophic bacteria comprising the heterologous nucleic acid molecule encoding the fatty acid converting enzyme is capable of converting a $C_1$ substrate under aerobic conditions into a $C_8$-$C_{24}$ fatty aldehyde, fatty alcohol, fatty ester wax, a hydroxy fatty acid, dicarboxylic acid, or a combination thereof, and wherein the encoded fatty acid converting enzyme comprises:
(a) a fatty acyl-CoA reductase capable of forming a fatty alcohol; or
(b) a fatty acyl-CoA reductase capable of forming a fatty aldehyde; or
(c) a carboxylic acid reductase; and
(d) a thioesterase; and/or
(e) an acyl-CoA synthetase.

33. The methylotrophic bacteria according to claim 32, wherein the host methylotrophic bacteria is selected from *Methylobacterium extorquens, Methylobacterium radiotolerans, Methylobacterium populi, Methylobacterium chloromethanicum, Methylobacterium nodulans*, or high growth variants thereof.

* * * * *